United States Patent
Castagnaro et al.

(10) Patent No.: US 9,357,786 B2
(45) Date of Patent: Jun. 7, 2016

(54) POLYPEPTIDE HAVING INDUCING ACTIVITY FOR THE DEFENCE AGAINST BIOTIC STRESS IN PLANTS, NUCLEOTIDE SEQUENCE ENCODING THE SAME, MICROORGANISM, COMPOSITIONS AND METHODS

(75) Inventors: Atilio Pedro Castagnaro, De Tucuman (AR); Juan Carlos Diaz Ricci, De Tucuman (AR); Nadia Regina Chalfoun, De Tucuman (AR); Josefina Racedo, De Tucuman (AR); Sergio Miguel Salazar, De Tucuman (AR)

(73) Assignees: UNIVERSIDAD NACIONAL DE TUCUMAN, San Miguel de Tucuman-PCIA, De Tucuman (AR); CONSEJO NACIONAL DE INVESTIGACIONES CIENTIFICAS Y TECNICAS (CONICET), Ciudad de Buenos Aires (AR)

( * ) Notice: Subject to any disclaimer, the term of this patent is extended or adjusted under 35 U.S.C. 154(b) by 175 days.

(21) Appl. No.: 14/005,532

(22) PCT Filed: Mar. 16, 2012

(86) PCT No.: PCT/ES2012/070173
§ 371 (c)(1),
(2), (4) Date: Nov. 25, 2013

(87) PCT Pub. No.: WO2012/123614
PCT Pub. Date: Sep. 20, 2012

(65) Prior Publication Data
US 2014/0212385 A1    Jul. 31, 2014

(30) Foreign Application Priority Data
Mar. 16, 2011 (AR) ................................ P110100854

(51) Int. Cl.
*C12N 1/20* (2006.01)
*C07H 21/04* (2006.01)
*A01N 63/04* (2006.01)
*C07K 14/37* (2006.01)
*C12R 1/745* (2006.01)

(52) U.S. Cl.
CPC ................ *A01N 63/04* (2013.01); *C07K 14/37* (2013.01); *C12R 1/745* (2013.01)

(58) Field of Classification Search
USPC .......................................... 435/222; 536/23.2
See application file for complete search history.

(56) References Cited

FOREIGN PATENT DOCUMENTS

CN            101235355 A         8/2008

OTHER PUBLICATIONS

Choi et al., "Biocontrol Activity of Acremonium strictum BCP Against Botryrtis Diseases," Plant Pathology Journal, vol. 25, No. 2, Jun. 2009, pp. 165-171.
Jallow et al., Indirect interaction between an unspecified endophytic fungus and a polyphagous moth,' Basic and Applied Ecology, vol. 5, No. 2, Jan. 1, 2004, pp. 183-191.
Ragazzi et al., "Antagonistic effects of some fungi of banana fruit against *Coletotrichum musae*," Zeitschrift Fuer Planzenkrankheiten Und Pflanzenschutz, vol. 104, No. 3, 1997, pp. 281-288.
Malmberg et al., "Identification of rate-limiting steps in cephalosporin C biosynthesis in Cephalosporium acremonium: a theoretical analysis," Applied Microbiology and Biotechnology, vol. 38, No. 1, Jan. 1, 1992, pp. 122-128.
Stergiopoulos et al., "Fungal Effector Proteins," Annual Review of Phytopathology, vol. 47, 2009, pp. 233-263.

*Primary Examiner* — Tekchand Saidha
(74) *Attorney, Agent, or Firm* — Muncy, Geissler, Olds & Lowe, P.C.

(57) ABSTRACT

Polypeptide having activity inducing pathogen plant defense, nucleotide sequence encodes it, microorganism, compositions and methods. The polypeptide is a subtilisin derived from a strain of *Acremonium strictum*. The polypeptide is encoded by the nucleotide sequence SEQ ID NO: 1 or sequences at least 90% homologous to the same and has the amino acid sequence SEQ ID NO: 2 or sequences at least 90% homologous to the same.

2 Claims, 15 Drawing Sheets

|  | A | B | C | D |
|---|---|---|---|---|
| Pre-treatment | Elicitor SS71 | BTH | SA | Water |
| $DSR_{40}$ | 1.2 | 1.2 | 1.5 | 5 |

N-terminal:    A-Y–T-T-Q-A-S-A-P-W
msms 1095.19   (residues 108-118 relative position with respect to the reference sequence of *Trichoderma koningii*). See FIGURE 19C.

msms 2441.2    V-L-S-D-S-G-S-G-S-T-S-G-I-I-A-G-I-N-Y-V-V-S-D-S-R
               (residues 204-229 relative position with respect to the reference sequence of *Trichoderma koningii*). See FIGURE 19C.

msms 1938.1    I-V-A-I-A-T-T-G-V-I-K-G-I-P-S-G-T-P- N- R
               (residues 362-381 relative position with respect to the reference sequence of *Trichoderma koningii*). See FIGURE 19C.

FIGURE 17

(SEQ ID NO: 1)

```
  1  GCGTACACCA CCCAGGCCAG TGCCCCCTGG GGTCTTGCCC GTATCTCTAC TCGTCAGCGT
 61  GGCCCAACTG GCTACACCTA CGACGACAGC GCCGGCGCAG GAACCTGCTC CTACATCATT
121  GACACCGGCA TCCAGGCTAA CCACCCCAAC TTCGGTGGCC GTGCTTTCCA GCTTGTCTCC
181  TACCAAGGCA GCAACGCCGA CGGTAATGGC CACGGCACTC ACGTTGCCGG TACCATCGGT
241  TCTACCACCT ACGGTGTCGC CAAGCGCACC ACCCTCCTCG GCGTCAAGGT CCTCAGCGAC
301  TCCGGCTCCG GTTCCACCTC CGGTATCATC GCCGGCATCA ACTACGTCGT CAGCGACTCT
361  CGCTCCCGCA GCTGCCCCAA CGGTTCCGTC GCCAACATGT CGCTCGGCGG AGGCTACTCT
421  GCTTCGCTCA ACAGCGCGGC CAAGTCCTTG ATCGACAACA ACATCTTCCT TGCCGTTGCT
481  GCCGGTAACG AGAACCAGAA CGCCGCCAAT GTCTCCCCTG CTTCTGAGCC GACTGTCTGC
541  ACTGTTGGTG CGACCACTTC TGCCGACGCC AAGGCTTCTT TCTCCAACTA CGGCTCCGGT
601  GTCGACATCT TCGCTCCTGG TCAGAGCATT CTATCCACCT GGATTGGCAG CAGCACCAAC
661  ACCATCTCTG GCACCTCCAT GGCTTCTCCC CACATCGCCG GTCTTGCTGC TTACCTTGCT
721  GGTCTTGAGG GCTTCCCCGG TGCCCAGGCC CTGTGCAACC GCATCGTCGC CCTCGCTACC
781  ACTGGTGTCA TCACCGGTCT GCCCAGCGGT ACCCCCAACC GCCTTGCCTT CAACGGCAAC
841  CCCTCTGGTT AAA
```

FIGURE 18A (SEQ ID NO: 2)

```
1    AYTTQASAPW GLARISTRQR GPTGYTYDDS AGAGTCSYII DTGIQANHPN FGGRAPQLVS
61   YQGSNADGNG HGTHVAGTIG STTYGVAKRT TLLGVKVLSD SGSGSTSGII AGINYVVSDS
121  RSRSCPNGSV ANMSLGGGYS ASLNSAAKSL IDNNIFLAVA AGNENQNAAN VSPASEPTVC
181  TVGATTSADA KASFSNYGSG VDIFAPGQSI LSTWIGSSTN TISGTSMASP HIAGLAAYLA
241  GLEGFPGAQA LCNRIVALAT TGVITGLPSG TPNRLAFNGN PSG
```

FIGURE 19A

POLYPEPTIDE HAVING INDUCING ACTIVITY FOR THE DEFENCE AGAINST BIOTIC STRESS IN PLANTS, NUCLEOTIDE SEQUENCE ENCODING THE SAME, MICROORGANISM, COMPOSITIONS AND METHODS

This invention refers to a polypeptide having inducing activity for the defense against biotic stress in plants, nucleotide sequence encoding the same, microorganism, compositions and methods. More specifically, this invention refers to a subtilisin polypeptide derived from *Acremonium strictum*, wherein such polypeptide has elicitory activity. According to a particular embodiment of the invention, the polypeptide is codified by nucleotide sequence SEQ ID NO: 1 or sequences being at least 90% homologous to the same, and has the amino acid sequence SEQ ID NO: 2 or sequences being at least 90% homologous to the same, wherein such polypeptide has elicitory activity.

BACKGROUND

Strawberry is a fruit with remarkable characteristics, which can be eaten fresh, dried, frozen or canned. From an economic point of view, strawberry is a very important culture because of the number of input and technology used, apart from the added value it can achieve due to the fact it can be industrialized and exported.

One of the main problems of producing strawberries is the great number of diseases and pests (biotic stress) that attack the cultivars thereof, which result in limitation to the fruit's production and quality. The main cause of biotic stress for strawberries is fungal diseases.

There are many diseases, the most frequent of which are as follows:

Root and crown rot: several diseases caused by fungi among the genus *Phytophthora, Rhizoctonia* and *Colletotrichum* (anthracnose).

Leaf diseases: *Xanthomonas fragariae* (angular leaf spot); *Gnomonia comari* (foliar spot); *Mycosphaerella fragariae* or Ramularia (leaf spot); *Diplocarpon earliana* (leaf burn or spot); *Dendrophoma/Phomopsis obscurans* (stain); *Sphaerotheca macularis* (oidium); *Colletotrichum* spp. (anthracnose).

Flower and fruit diseases: *Rhizopus stolonifer* (rot); *Botrytis cinerea* (grey mould); *Colletotrichum* spp. (anthracnose).

Strawberry anthracnose, caused by a *Colletotrichum* fungal complex, is definitely the disease that most adversely affects the culture thereof, attacking almost every organ in the plant and originating great loss both in fruit production and greenhouses (seedling production), mainly in tropical and subtropical agro-climatic regions.

As a result of the wide pathogenic diversity (at least three different species), almost all kinds of strawberries are sensitive to anthracnose. In terms of culture's genetic enhancement, it is difficult to combine in a single variety genes conferring certain characteristics regarding production, greenhouse management, and resistance to diseases, and even more difficult to a disease caused by different pathogens such as anthracnose.

Culture management together with chemical treatments help reducing anthracnose incidence. However, the excessive use of agrochemicals has a high impact on the ecosystem's degradation and on farm worker's health, as well as on water pollution and on the content of toxic residues in food, apart from favouring the origination of fungicidal-resistant fungi strains and having direct effects on the elimination of pests' natural enemies. The excess of fungicidal residues in the fruit can cause serious problems when marketing or exporting strawberries for not meeting the quality standards required by local authorities or importing markets.

There is currently a major global agreement as to promoting, in general, responsible or sustainable agriculture through the development of productive systems integrating low-environmental impact agronomic procedures (integrated production). Among the different biological approaches encompassed within the term biotechnology, the use of varieties with increased resistance (resulting from conventional or molecular biotechnology-assisted genetic enhancement) as well as Biological Control Agents (BCA) is included.

BCAs may (i) act directly on the pathogen such as in the case of "antagonist microorganisms"; (ii) exert an indirect action by interacting in the host plant, providing protection against a disease, either by: hypovirulence transmission to virulent races thereby neutralizing such disease, or (iii) by activating the plant's defense mechanisms, known as "Induced Resistance" or "preimmunization".

Plants defend themselves from potential invading pathogens either through morphological structures acting as physical barriers that inhibit the pathogen's entrance and development, or by biochemical reactions occurring in different plant tissues producing toxic substances for the pathogen, or creating conditions that inhibit the microorganism's entrance and development in the host. Such defenses may be either part of the plant being a non-specific protection against a wide range of microorganisms or induced in the presence of the attacking pathogen. In this latter case, plants as well as other living beings activate their own defense systems as they recognize a pathogenic-microorganism-derived molecule or else as they detect any molecule generated during the pathogen's invasion, any of them being referred to as defense "inducer" or "elicitor".

In plant/pathogen interactions, inducing molecules alert of the presence of the invading pathogen when the pathogen is recognized by the host plant (Nürnberger, 1999. Cell Mol. Life Sci. 55, 167-182). In early recognition of the elicitors of the attacking pathogen, the plant produces a rapid activation of its defense mechanisms, which block the infection, stopping the pathogen's progress. In this case, the plant/pathogen interaction is said to be incompatible because it does not result in a disease, the phytopathogen strain being defined as non-virulent (Keen, 1990. Annu. Rev. Genet. 24, 447-463). In contrast, the plant develops the disesease when it is unable to detect the pathogen's aggression or when it detects it late (the elicitors thereof), and in spite of triggering certain defense mechanisms, they are not sufficient to timely stop the invasion, thus the plant/pathogen interaction is said to be compatible and the strain is deemed virulent.

During a fungal infection, plants can recognize the aggressor via a set of elicitors. Some of the inducing molecules are derived from the pathogen (non-self factors) and can be present at the fungal surface (e.g., chitin and glucan fragments) or secreted by the pathogen (e.g., avirulence proteins); while other molecules are generated by the plant during the fungal invasion (known as self factors), such as in the case of plant cell wall fragments (e.g., oligogalacturonates, chitin, heptaglucans, monosilated glycopeptides) released from polymeric precursors by action of the invading pathogen's hydrolytic enzymes (Knogge, 1996. The Plant Cell 8, 1711-1722). Thus, elicitors can be classified as pre-formed compounds, which are present on the pathogen's surface, or as induced, as when synthesized during the interaction between the pathogen and the host plant.

In general, the pathogen recognition and the subsequent activation of resistance responses to disease in plants can occur at a species level (e.g., species or non-host resistance, or cultivar non-specific host resistance, or innate immunity) or at a genotype level (cultivar specific host resistance). A cultivar's specific resistance is expressed in a given cultivar against one or a reduced number of pathogenic races and represents what is known as "gene to gene" response, being genetically determined by the complementary pair codified by the pathogen avirulence (Avr) gene and the product from a plant resistance (R) gene.

Thus, when the AVR protein is directly or indirectly recognized by a resistant host plant, it acts as a defense "specific elicitor", and can be detected by the plant surveillance system. However, innate immunity is the prevailing resistance form in all plants species. In this response, a great variety of products associated to so-called "general elicitor" microorganisms, induce the defense response in many plant species and do not depend on a specific cultivar. The term "Pathogen-Associated Molecular Pattern" (PAMP) refers to any molecule capable of activating the plant defense system, and it can be found in a wide range of pathogens (Bent and Mackey, 2007. Annu. Rev. Phytopathol. 45, 399-436). Kamoun (Kamoun, 2006. Annu. Rev. Phytopathol. 44, 41-60) reports the elicitors produced by plant pathogenic oomycetes fungi, while Stergiopoulos et al. (Stergiopoulos and de Wit, 2009. Annu. Rev. Phytopathol. 47, 233-263) describe fungal avirulence proteins reported so far.

After the recognition of the elicitor, a series of cytological shifts and biochemical responses in plant cells have been identified. In biochemical terms, it can be said that an inducer interacts with one receptor on the cell surface which detects the extracellular signal converting it in intracellular signals, the transduction of which imply (a) ionic trans-membrane fluids (i.e. entrance of $Ca^{2+}$, $H^+$ and $Cl^-$); (b) production of reactive oxygen species (ROS) such as $H_2O_2$, $O_2^-$, etc., toxic for the cells, producing "oxidative burst"; (c) nitric oxide production (NO); c) phosphorylation/dephosphorylation of mitogen-activated protein kinases (MAPKs) and other calcium dependant protein kinases (CDPKs).

These signals give rise to early defense responses at the infection site, and late defense responses in distant plant areas.

Local defense responses to elicitors imply regulating several genes, which contribute to generate protective physiological conditions against invading pathogens. At the infection site, such responses include generation of reactive oxygen species (ROS), rapid accumulation of several enzymes and metabolites, such as for example, proteins involved in the production of signals, such as salicylic acid (SA), jasmonates and/or ethylene, and of enzymes related to phenylpropanoid metabolism (PAL: phenyl ammonium-lyase; CHS: chalcone synthase; etc.) and phytoalexin biosynthesis, low molecular weight secondary metabolites having antimicrobial activity, and the so-called PR proteins (Pathogenesis Related Proteins). Such defense is restricted to the area surrounding the pathogen penetration site.

In some cases, cells at the infection site can undergo a process of cell death, which usually becomes visible as a hypersensitive response. Hypersensitive Response (HR) consists in the rapid and localized death of the host cells invaded by the pathogen, by a necrosis phenomenon or programmed cell death (PCD). This phenomenon is associated with reinforcement in the cell wall of affected cells by local lignifications and callose accumulation, cross-linking of hydroxyproline-rich glycoproteins (HRGP), activation of the enzymes implied in molecule cross-linking as a plant strategy to limit the colonization to infection sites.

Salicylic acid (SA), is a plant hormone which among other functions inhibits catalase aggravating oxidative stress, and also coordinates the expression of PR protein subgroup which are divided in three classes: chitinases, glucanases and chitin binding proteins. In summary, to kill or successfully stop an invading microorganism a special and accurately timely coordination of induced defense responses is required.

A local infection often leads to induction of similar defense responses in non-infected plant tissues thus resulting in resistance to subsequent infections (Kuć, 1982. BioScience 32, 854-860). This line of defense leads to the accumulation of proteins and hydrolytic enzymes throughout the organisms, thus being referred to as "systemic" (Hunt and Ryals, 1996. Crit. Rev. Plant Sci. 15, 583-606). It usually provides resistance to the primary inducing agent (virulent pathovar) and also to a wide range of other fungal, bacterial and viral pathogens (immunization). When this defense response is mediated by action of an avirulent pathogen, it is referred to as "Systemic Acquired Resistance" (SAR). Furthermore, systemic resistance may also be triggered by a rhizosphere non-pathogenic microorganism, and in this case it is referred to as "Induced Systemic Resistance" (ISR); or it may be induced by injuries (mechanical damage).

The different systemic defense responses associated with pathogen infections include induction of several PR genes, accumulation of phytoalexins, induction of EROs and micro-HR.

The foregoing suggests that the induction of a broad-spectrum systemic defense response (either SAR or ISR) can be used as "immunization" strategy in order to prevent or reduce crop diseases (Induced Resistance or IR). For strawberries, the use of IR for controlling *Phytophthora* spp. (Eikemo et al., 2003. Plant Dis. 87, 345-350) and *Botrytis* (Adikaram et al., 2002. *Australasian Plant Pathology* 31(3), 223-229) has been suggested. This host plant protection phenomenon which was originally referred to as "Cross-protection" was used as means of management of virus-caused diseases by prior inoculation with weak strains of the same virus, thus making that the virus inoculated first prevent the development of the subsequent virus. Then, it was apparent that it was also possible to increase resistance to fungal pathogen severe races by pre-inoculation with an avirulent genotype of the same fungus species or by application of a rhizosphere non-pathogenic microorganism; as mentioned above, this last phenomenon was called ISR as opposed to SAR.

Unlike the response induced by a rhizosphere non-pathogenic microorganism, field implementation of a SAR-like system, which implies direct plant infection with a live pathogenic microorganism, is not possible, since it poses serious problems, among which it is worth mentioning that it is possible that an avirulent strain used to protect a cultivar can produce the disease in other susceptible genotypes (Fulton, 1986. Annu. Rev. Phytopathol. 24, 67-81). A biotechnological option to solve this problem and induce resistance involves inactivating the pathogen and applying portions from different pathogenic cultures (non-pathogenic extracts) that retain inducing defense activity, which at the same time lose pathogenic potential, that is, using fractions of the inactivated pathogen containing the defense inducing agent(s). Having greater knowledge of the system will allow for the direct application of elicitor molecules derived from the plant/avirulent pathogen interaction, capable of providing resistance against diseases through the induction of a broad-spectrum systemic defense response (SAR elicitor), to the expression of such pathogen avirulent gene in transgenic plants.

Very few elicitors that can effectively induce resistance are currently known. In strawberries, registered biopesticides with elicitory action include harpin proteins (trade name: MESSENGER®), an alternative to the use of methyl bromide, which is effective against bacterial leaf spot, tristeza caused by bacteria, bacterial blight, certain fungal diseases; and chitosan (trade name: ELEXA-4®) which is active against woolly aphids and powdery "mildew" and grey mould. However, until now, no type of biological control method to control anthracnose (*Colletotrichum* spp.) in strawberries has been suggested.

In light of the above mentioned, having determined the lack of solutions with respect to the provision of new disease treatment and/or prevention methods, the inventors herein have identified a new protein excreted to the medium by *Acremonium strictum*, and having purified it to homogeneity. This protein acts as avirulence factor (elicitor), triggering different defense mechanisms immunizing the plant, thus making it resistant to diseases, such as anthracnose produced by *Colletotrichum* spp.

SUMMARY OF THE INVENTION

A subtilisin polypeptide having elicitory (inducing) activity of the defense against biotic stress in plants, the polypeptide being derived from *Acremonium strictum*, for example *Acremonium strictum* SS71 deposited in the German deposit center DSMZ under access code DSM 24396, and having elicitory activity is provided. The polypeptide is codified by nucleotide sequence SEQ ID NO: 1 or sequences at least 90% homologous to the same, and having the amino acid sequence SEQ ID NO: 2 or sequences being at least 90% homologous to the same, wherein such polypeptide has elicitory activity.

A nucleotide sequence encoding the elicitor polypeptide shown in sequence SEQ ID No: 1 or sequences at least 90% homologous is provided.

An elicitor polypeptide producing microorganism is provided, such microorganism being the strain of *Acremonium strictum* SS71 deposited in the German deposit center DSMZ under access code DSM 24396.

A composition useful for inducing resistance to biotic factors in plants is provided, the composition comprising *Acremonium strictum* conidia and excipients, e.g. comprising between $1\times10^3$ and $1\times10^8$ conidia/ml. Prefererably, the composition comprises conidia of the strain of *Acremonium strictum* SS71 deposited in the German deposit center DSMZ under access code DSM 24396.

A composition useful for inducing resistance to biotic factors in plants is provided, the composition comprising *Acremonium strictum*. Preferably, the composition comprises an extract of the strain of *Acremonium strictum* SS71 deposited in the German deposit center DSMZ under access code DSM 24396. The extract can be cell-free supernatant or conidial extract.

A composition comprising between 2.5 and 15 µg/ml of elicitor polypeptide is provided.

A procedure for obtaining and purifying the elicitor polypeptide is provided, comprising the following steps:
(a) culturing *Acremonium strictum*, preferably *Acremonium strictum* SS71 under access code DSM 24396;
(b) recovering the supernatant;
(c) concentrating the supernatant; and
(d) ultrafiltrating the product obtained in the previous step.

A method for inducing resistance to pathogens in plants is provided, comprising the application to such a plant of a composition derived from *Acremonium strictum*, e.g. the strain of *Acremonium strictum* SS71 under access code DSM 24396. The composition can be: a conidial suspension of the strain, a cell-free extract, a conidial extract, a culture supernatant, an elicitor polypeptide solution or a combination thereof. The conidial suspension can be applied at a concentration from between $1\times10^3$ and $1\times10^8$ conidia/ml, the cell-free extract can be at a concentration between 1.4 and 9 µg protein/ml, the conidial extract can be at a concentration between 0.12 and 1.5 µg protein/ml and the elicitor polypeptide solution can be between 2.5 and 15 µg/ml. Since the elicitor generates a non-specific systemic response, the method of the invention provides protection against a wide range of pathogens, being effective for fungal, bacterial and viral protection. The method can be applied among others to the following pathogens: *Colletotrichum* spp., *Botrytis cinera* or *Xanthomonas fragariae*. Moreover, considering the protection mechanisms triggered by the elicitor are widely spread in the plant kingdom, the method is effective for any type of plant, in particular eudicotyledons, such as strawberry (*Fragaria×ananassa*), tomato (*Solanum lycopersicon*) or *Arabidopsis thaliana*, by aspersion in the aerial parts, infiltration or irrigation.

DESCRIPTION OF THE DRAWINGS

FIG. 1 shows in a graphic the disease severity level (DSR) of anthracnose in strawberry plants cv. Pajaro treated with extracts containing the elicitor 48 hours prior to inoculation with virulent isolate M11 of *C. acutatum*. Plants were assessed 40 DAI (Days After Inoculation) with M11. CE: Conidial extract (10 µg protein/ml) obtained by sonication; SN: liquid culture supernatant grown in PG (potatoe-glucose) medium to stationary phase (10 µg protein/ml). Ctr-PC: M11-infected plant control, which were previously inoculated with the avirulent strain (SS71) of *A. strictum*. Ctr.-Ca: M11-infected plant control without previous treatment. DSR means Disease Severity Rating.

FIG. 2A shows heat susceptibility of elicitory activity. Assays were carried out with concentrated and dialysed culture supernatants of isolate SS71 of *A. strictum* grown in PG medium to stationary phase. (A) SN: extract without treatment. SN1: extract heated until boiling in boiling water bath for 15 min.; SN2: extract heated to 120° C. by autoclaving (overpressure 1 atm.) for 15 min. FIG. 2B shows susceptibility of elicitory activity to digestion with Proteinase K. SN: extract without treatment; SNA: extract treated with Proteinase K (100 µg/ml) for 1 hour at 50° C.; and SNB: extract treated for 12 hours at 50° C. Controls: Ctr.-PC: M11-infected plants which were previously inoculated with the avirulent strain (SS71) of *A. strictum*. Ctr.-Ca: M11-infected plants without previous treatment. Assays were conducted 40 DAI. DSR means Disease Severity Rating.

FIG. 3 shows the first purification step of the fungal elicitor of the invention in a profile obtained from FPLC chromatographical separation using an anion exchange Q matrix balanced at 7.5 (Pharmacia). Elution was performed with discontinuous increasing NaCl gradient (0-100%). The activity is concentrated in peak I.

FIG. 4 shows the second purification stage of the fungal elicitor of the invention in a profile obtained from FPLC chromatographical separation using an hydrophobic interaction matrix Phenyl Superose HP (Pharmacia) balanced with Tris-HCl (50 mM, pH 7.5), EDTA (1 mM) and $(NH_4)_2$ SO$_4$ (1.5 M), and eluted with discontinuous decreasing (NH$_4$)$_2$ SO$_4$ gradient (100-0%). The activity is concentrated in pool IV.

FIG. 5 shows proteins present in fractions I to IV (20 μg total charge) obtained by FPLC in Phenyl Superose HP (FIG. 4) separated by SDS-PAGE at 12%. The activity is concentrated in pool IV. The arrow indicates the active elicitor protein post-purified to homogeneity (FIG. 6).

FIG. 6 shows SDS-PAGE at 10% of the active subfraction (7 μg total protein) obtained by re-chromatography of pool IV via Phenyl Superose HP eluted under the same conditions as mentioned in FIG. 4, with a gradual (NH$_4$)$_2$SO$_4$ inverse gradient (100-0%). The active protein elutes from the Phenyl Superose HP column at a concentration of (NH$_4$)$_2$SO$_4$ of 0.5 M.

FIG. 7 shows a picture of plants treated and non-treated with the elicitor of the invention (2.5 μg protein/ml) and after infection with the virulent isolate (M11) of C. acutatum at 40 days post-inoculation. The top row depicts the plants pre-treated with the elicitor and the bottom row depicts the plants treated with water (virulence control) respectively, 48 h before inoculation with pathogen M11.

FIG. 8 shows pictures of the accumulation of reactive oxygen species (ROS) 4 h after treatment by elicitor aspersion (10 μs protein/ml) in leaves of strawberry cv Pajaro. (A) H$_2$O$_2$ accumulation detected by DAB (diaminobenzoic acid method (B) O2 accumulation (superoxide anion) detected by NBT (nitroblue tetrazolium method) and (C) control of water-treated leaf. Scale bars indicate 100 μm.

FIG. 9 shows pictures of accumulation of self-fluorescent species after treatment by elicitor infiltration (50 μl, 10 μs protein/ml) in strawberry cv. Pajaro leaves. (A) Leaf treated at time zero or treated with water, (B) fluorescence 12 hours after treatment and (C) fluorescence 72 hours after treatment. Pictures were taken in a fluorescent magnifier (320 nm, Leitz). Scale bars indicate 300 μm.

FIG. 10 shows pictures of the accumulation of callose in strawberry cv. Pajaro leaves 7 days after treatment by aspersion with the elicitor (10 μg protein/ml; A) or water (control; B); or 2 days post-inoculation with the virulent isolate of C. acutatum M11 treated 7 days before with elicitor (10 μg protein/ml; C); and control of plants only infected with M11 (D). Scale bars indicate 100 μm.

FIG. 11 show a graph depicting accumulation of salicylic acid in strawberry cv. Pajaro leaves after treatment by aspersion of water ☐, BTH (S-methyl benzo[1,2,3]thia-diazole-7-carbothiate acid) an analogue to SA (0.5 mM) ▫ and elicitor (15 μg protein/ml) ■.

FIG. 12 shows the experimental scheme, the aspect of strawberry cv. Pajaro plants after different treatments and the DSR values after 40 DAI. One of the plants' leaves was treated with the elicitor (arrow) 7 days before infecting the rest of the aerial part by aspersion of the virulent isolate M11 of C. acutatum (1.5×10$^6$ conidia/ml). (A) plants pre-treated with elicitor (5 μs protein/ml), (B) plants pre-treated with BTH (0.5 mM), (C) plants pre-treated with SA (0.5 mM) and (D) with water. DSR means Disease Severity Rating.

FIG. 13 shows a graph depicting the disease's symptomathology in several strawberry cultivars pre-treated with the elicitor (10 μs protein/ml) derived from A. strictum SS71. DSR means Disease Severity Rating.

FIG. 14 shows a graph depicting NO (nitric oxide) and ROS (H$_2$O$_2$) production measurements in tomato (Solanum lycopersicon) cell culture by fluorescent probes. DAF-FMDA fluorescent probe was used for NO detection and H2DCF-DA probe was used for ROS detection, in both cases λ exi=480 nm; λ emi=525 nm. Incubation time was 30 minutes at room temperature. The elicitor was used at a concentration of 10 μg/ml for NO and 5 μg/ml for ROS; xylanase (inductor control) at 100 μg/ml for NO and 10 μg/ml for ROS.

FIG. 15 shows pictures of the maximum production of intracellular hydrogen peroxide with Dichlorofluorescin diacetate (DCFH-DA) fluorescent probe in Arabidopsis thaliana leaves observed by fluorescent microscopy (UV-light). Pannel (A) corresponds to foliar tissue, control of plants treated by aspersion with water 2 hpt (hours post treatment) while panel (B) corresponds to treatment with elicitor at the same time (2 hpt). Scale bars indicate 100 μm.

FIG. 16 shows pictures depicting evolution through time of superoxide radical generation as detected by dyeing with NBT in Arabidopsis thaliana leaves treated with elicitor 2 hpt (A), 4 hpt (B) and 6 hpt (C), and the respective controls thereof (treated with water) at each time (D-F).

FIG. 17: FIG. 17 shows the amino acid sequences (Edman method) of the three analyzed fragments (triptych digestion) of the 34 kDa defense elicitor polypeptide of the present invention isolated from A. strictum.

FIG. 18 shows the nucleotide sequence encoding the polypeptide with elicitory activity of the present invention, A: Full nucleotide sequence of mature transcript or complementary DNA (cDNA) (SEQ ID NO: 1); B Nucleotide sequences producing the maximum similarity values and source species thereof by Blast X.

FIG. 20 shows absorbance shifts at λ=405 nm over time. The curves indicate the proteolytic activity of elicitor protein at 15 μg/ml (▲) and subtilisin of Bacillus subtilis (0.04 μg/ml) used as positive control (■). Curve (♦) indicates the self-proteolysis activity of the chromogenic substrate. Absorbance increase is due to the enzymatic reaction of proteolysis of chromogenic sustrate N-Suc-Ala-Ala-Pro-Phe-p-NA by realeasing p-NA (λ=405 nm).

DETAILED DESCRIPTION OF THE INVENTION

Definitions

Figure 1:
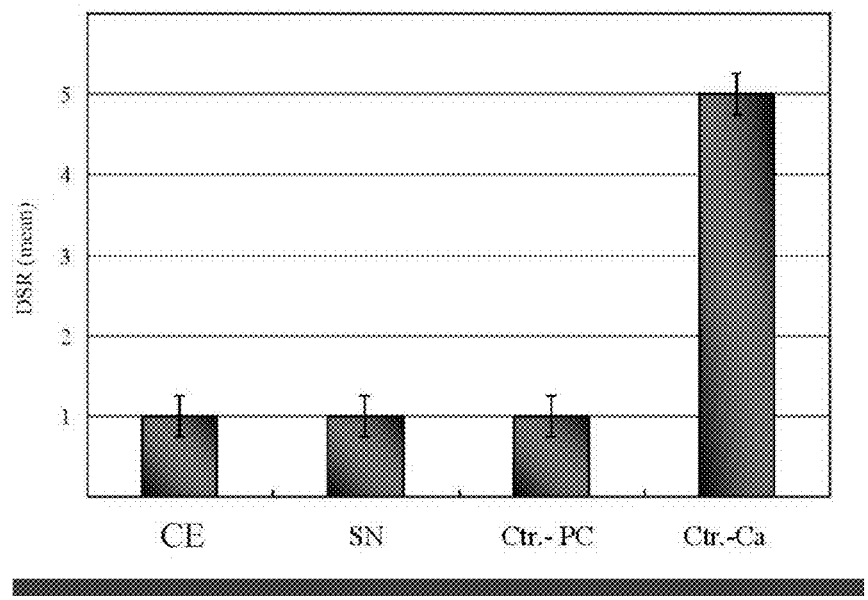
FIG. 1.
Figure 2:
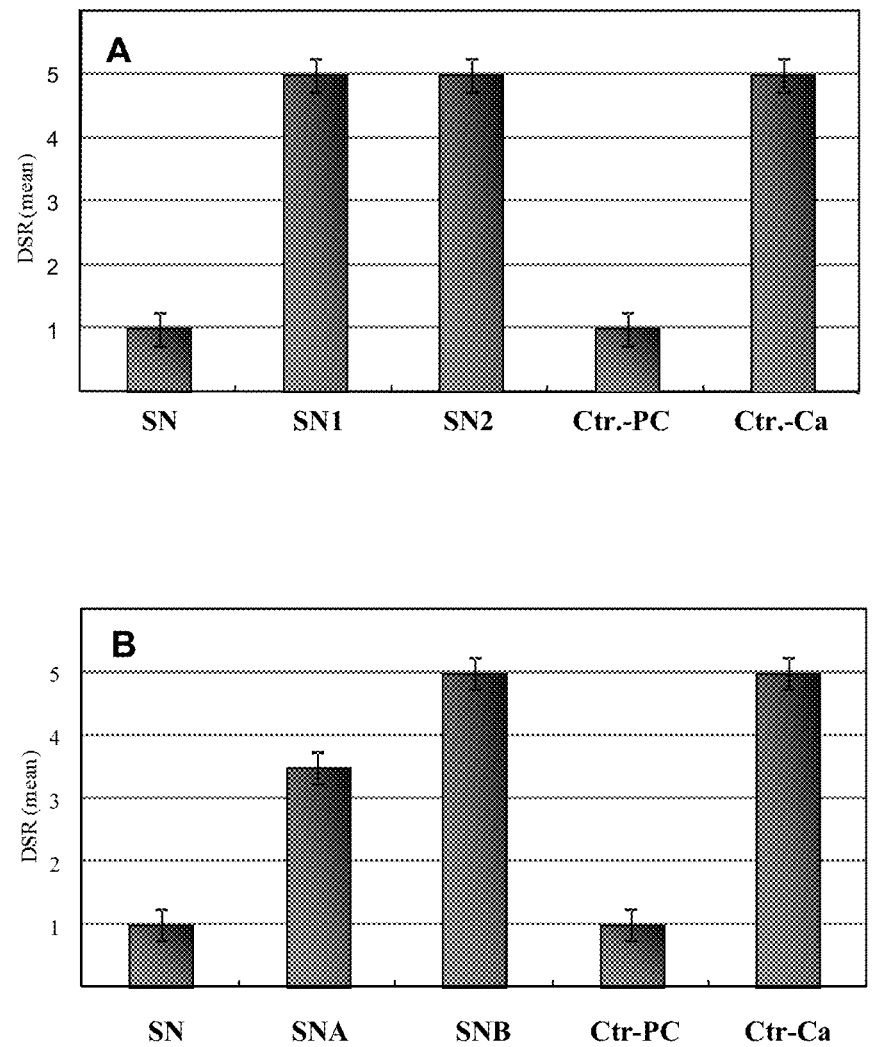
FIG. 2.
Figure 3:
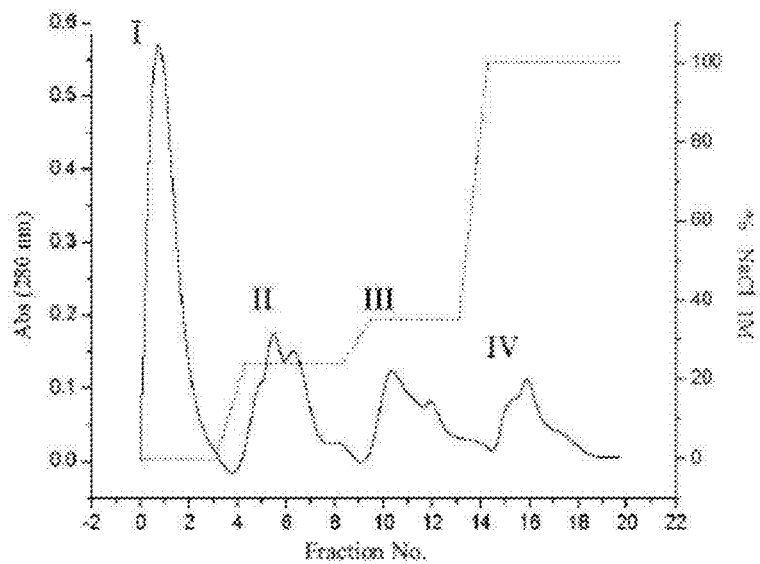
FIG. 3.

For the purposes of the present patent application, the terms "elicitor or elicitors" refers to any compound capable of inducing any type of defense response in a plant. Elicitors can be molecules of very different kind: proteins, carbohydrates, lipids; small peptides, small compounds of heterogeneous origin, such as secondary metabolites, sugar and/or amino acid derivatives, fatty acids and combinations thereof.

Elicitory Capacity has the same meaning as inducing activity of the defense against stress in plants, e.g., biotic stress.

On the other hand, as used herein "Induced Resistance" (IR), refers to the phenomenon whereby a plant subjected to the appropriate stimulation of its defense by previous exposure to an elicitor acquires an increased level of resistance against pathogens.

Anthracnose is a fungal disease that produces holonecrosis in the vegetative part of the plant. The infective form of Colletotrichum spp. species causing anthracnose is conidia which, upon germination, penetrate through stomas, tricomas, or directly through the plant leaves epidermis and attack the conducting tissue (xylem), causing petiole girdling. Symptoms start to appear in petiole's upper portion and proceed to attack the crown (modified stem), resulting in the death of the plant. Assessment on the severity of anthracnose symptoms is performed in the petiole according to the scale set by Delp and Milholand (Delp and Milholand, 1980. Plant Dis. 64, 1071-1073) which defines a Disease Severity Rating (DSR). This DSR scale ranges from 1 to 5 increasing in accordance with the severity of the disease symptoms as determined in the petiole. The different severity levels are classified as follows:

Infection Degree #1: without lesions.
Infection Degree #2: lesions shorter than 3 mm long and shallow, dark stains along the petiole (small black spots).
Infection Degree #3: lesions between 3-10 mm long, dark stain generally surrounded by red colour.
Infection Degree #4: severe lesions and girdling of petiole, which can affect up to 50% of its length.
Infection Degree #5: very severe lesion, with girdling of petiole, which can affect more than 50% of its length and/or dead plant.

The protocol used to evaluate anthracnose evolution in the present application was as follows:

(1) Lesions are assessed in the petioles of the three fully expanded youngest leaves.

(2) In case there are several degrees of symptoms in the same plant, the maximum degree at the time of observation is used.

(3) Disease symptoms are assessed 9, 21, 30, 40 days after inoculation (dpi: days post-inoculation) with the virulent pathogen, in accordance with the enhanced procedure by Salazar et al., 2001 (REDBIO Brasil) and 2002 (REDBIO Argentina).

For practical and simplicity purposes when presenting the results in the present application, only the degrees of the symptoms 40 days after inoculation (40 dpi) for each phytopathological assay are informed herein.

Disease evolution and full recovery of the plant lot were considered as assessment standards. Plant recovery is determined by the DSR at the end of the assessment, i.e., 40 days ($DSR_{40}$), wherein:

$DSR_{40}$=1, full recovery or lack of disease.
$DSR_{40}$=2, partial recovery.
$DSR_{40}$=3 a 5, disease persistence.

Plant recovery gives a measurement of the efficiency of the inducer protection regarding the product used in the plant treatment.

This application provides an elicitor that enables the prevention and/or treatment of plant diseases, such as anthracnose. More particularly, the present invention provides a polypeptide codified by nucleotide sequence SEQ ID NO: 1 or sequences at least 90% homologous to the same. In a preferred embodiment, such polypeptide comprises amino acid sequence SEQ ID NO: 2 or sequences at least 90% homologous to the same, wherein such polypeptide has elicitory activity. In another more preferred embodiment, the polypeptide of the present invention is derived from a strain of *Acremonium strictum*, preferably such strain is the strain *Acremonium strictum* SS71, deposited pursuant to the Treaty of Budapest on Dec. 14, 2010 at the German deposit centre DSMZ under access code DSM 24396.

The polypeptide of the present invention was obtained after assessing several local isolates of different fungal pathogenic strains of strawberries from the North West region of Argentina, many of which correspond to the different species of *Colletotrichum* comprising the fungal complex responsible for anthracnose in the culture of strawberries: *C. fragariae*, *C. acutatum*, *C. gloeosporioides*. As a result of this assessment, the strain SS71, identified as *Acremonium strictum* which is the object of the invention, was isolated and purified, being virulent for some strawberry cultivars (i.e. cv. Chandler), while it is completely avirulent for other strawberry cultivars such as strawberry cv. Pajaro. Strain SS71 of *Acremonium strictum* expresses a polypeptide having an amino acid sequence SEQ ID NO: 2 or sequences at least 90% homologous to the same, wherein such polypeptide has elicitory activity.

From the analysis carried out in the different isolates, it can be seen that the plant/pathogen interaction is highly specific, i.e., it depends on the genotype of the plant and of the pathogen (pathovar or race). Different pathovars can affect a certain strawberry genotype in different severity degrees, and vice versa, different strawberry cultivars and varieties thereof respond in different ways when challenged with the same pathogenic isolate.

A Cross-Protection system in cv. Pajaro between avirulent isolate *A. strictum* SS71 and a virulent isolate of *C. acutatum* (M11) was established. For example, this system became apparent inoculating firstly the aerial parts of healthy plants with live conidia of isolate SS71 and after three days with live conidia of isolate M11, observing that no disease was produced. Cells in conidial state were used.

It is also shown that cv. Pajaro plants after infection with *A. strictum* SS71 acquire resistance against virulent strains of *Colletotrichum* spp., *Botrytis cinera* and *Xanthomonas fragariae*. It was also found that this protection is produced as a result of the interaction between cultivar Pajaro and the avirulent pathovar, inducing a SAR-type response.

This finding has interesting implications to generate an agronomical management of culture diseases, with minor impact on human and environmental health.

In a preferred embodiment, field implementation of an agronomical biocontrol system can be performed based on cross-protection, inoculating plants directly with the living strain or conidia of SS71 of *A. strictum*. Considering that even though the strain is avirulent against cv. Pajaro, it is capable of inducing disease in susceptible varieties, it is desirable to obtain non-pathogenic extracts containing elicitory capacity to produce formulations that trigger the defensive response, and it is better to obtain and use the compound having elicitory activity in order to prepare a composition for inducing a plant's defense system.

Another preferred embodiment is applying directly the elicitor molecule of the present invention to immunize and prevent fungal diseases of cultures, such as strawberry. Apart from being environmentally safe, this technology can further be an agronomically applicable alternative because it is harmless.

Cross-protection was observed against *C. acutatum* M11 previously inoculating cv. Pajaro plants with a suspension of live conidia of strain SS71 of *A. strictum* at a concentration of $1.5 \times 10^6$ conidia/ml.

In addition, the conidial extract of *A. strictum* SS71 obtained by sonication (CE) was analyzed and the evolution of disease symptoms was analyzed (DSR) over time (dpi) in double-treatment assays. Disease symptom analysis was done using the extremes, 1 when there was full recovery (lack of anthracnose symptoms) and 5 when there was no recovery.

When plants were sprayed with conidial extract obtained by cellular sonication to disrupt cells (CE), disease symptoms degrees similar to those of Cross-Protection controls were achieved, showing the same full recovery (DSR=1) after 40 days, similar to such controls (FIG. 1); i.e. CE shows high efficiency protection against the virulent strain causing anthracnose disease. This result indicates that: (a) the presence of live conidia of the avirulent pathogen (*A. strictum* SS71) of the invention is not required to trigger the resistance against the virulent pathogen (*C. acutatum* M11); (b) the medium containing conidia of the pathogen, inactivated by cell lysis physical treatment, is capable of retaining inducing activity present in such conidia in active state with equal protection efficiency.

The presence of the active agent in the liquid culture supernatant of the avirulent pathogen of *A. strictum* of the invention grown under optimal conditions to stationary phase was analyzed. For this purpose, a conventional potatoe-glucose (PG) medium was used and the activity present in the cell-free supernatant (SN) was measured. It was seen that the supernatant of the culture grown in the PG medium (SN) reaches DSR=1 at 30 days, a value kept during the entire assessment period ($DSR_{40}$=1; FIG. 1), thus, SN treatment leads to early full recovery of plants. This means that SN develops maximum protection efficiency ($DSR_{40}$=1) in the same way as the Cross-Protection control. This result indicates that activity with maximum protection efficiency is obtained from the liquid culture supernatant, implying that the active ingredient would be excreted to the culture medium.

Based on the above-mentioned results, it is seen that maximum protection efficiency is obtained from all assayed fractions of *A. strictum* SS71 of the invention, (DSR=1), in the same way as Cross-Protection control with CE and SN, thus it is concluded that they both present highly effective protection activity. These experiments confirm that the "inducing power" can be recovered in CE and SN portions, with which maximum protection is attained.

The protocol and experimental design used to assess the protection activity in the different fractions obtained (CE and SN) are detailed in Table 2 (see examples).

In order to characterize the elicitor, the chemical nature of the active ingredients and technological possibilities thereof were determined. The thermal stability of the elicitory activity was analyzed. For this purpose, the supernatant SN containing the active ingredient compound with "inducing power" at a high purity degree was used. In this sense, the SN was subjected to two thermal treatments with different intensity: (A) heating to boiling (100° C.) for 15 minutes (SN1), being sufficient for large proteins (in general, molecular weight greater than 10,000 Da) to be denaturalized, and insufficient to destroy other compounds of different chemical nature, such as carbohydrates, lipids, etc.; and (B) autoclaving (121° C.) for 15 minutes (SN2), being a more severe treatment which destroys the majority of compounds except for low molecular weight metabolites resistant to high temperatures, thermoresistant peptides, etc.

FIG. 2A shows the results indicating that the supernatant subjected to both thermal treatments generates an evolution of the disease which is very similar to the *C. acutatum* M11 positive control. Both SN1 and SN2 as well as the virulent strain control show, DSR=5; in the case of the heated supernatants such rating is achieved after 30 days, while in positive control it is reached after 21 days. In all cases, plants die after treatment. From this it is concluded that the defense inducing activity is practically completely lost upon severe heat exposure.

As shown in FIG. 2B, the same effect is seen when the SN is incubated with Proteinase K overnight (12 hours) under optimal conditions for such enzyme activity (50° C.), which is broadly used for proteolytic digestion.

The results shown indicate that the main active compound participating in the induction of the defensive response loses its activity not only because of the less severe thermal treatment (heating at 100° C. for 15 minutes), probably by cleavage of peptide bonds, but also by action of a protease (Proteniase K), thus concluding that it is a compound of protein nature.

For a better understanding of the obtention procedure of the polypeptide of the present invention, an example embodiment is described herein to attribute the protection effect against *C. acutatum* associated with the full supernatant derived from the avirulent pathovar of *Acremonium strictum* (isolate SS71) of the invention to a single purified molecule. In this case, firstly the extracellular protein/s with inducing activity was/were identified. In order to do so, a purification protocol was designed and optimized to recover the protein in large quantities and of high purity degree (single band on SDS-PAGE or single peak on FPLC), to obtain such a protocol experiments were performed in 2 steps:

(a) Optimizing the Fungal Culture Conditions for Maximum Production of Elicitory Activity.

Plant full protection is achieved by pre-treatment of plants with the axenic culture supernatant of the isolate *Acremonium strictum* SS71 in PG medium (potatoe-glucose, non-buffered, initial pH=6.75), grown at 28° C., in static form (no stirring), with continuous white light until reaching the to stationary growth phase (21 days). Total protein content in the final supernatant was 8.43 μg proteins/ml.

(b) Isolating the extracellular protein with inducing activity form PG medium:

As shown in the examples, the activity in each purification step was followed by two parallel methods: (a) ROS production ($H_2O_2$ and $O_2^{.-}$) 4 h post-, and (b) protection against the virulent isolate M11 of *C. acutatum.*

The purification protocol includes the following steps:

I. Initial Processing for Conservation:

To remove the mycelium, cultures were centrifuged at 16,300 g, for 30 minutes, at 4° C. The supernatant was recovered and filtered through diathomea earth and then through a filtering membrane with a pore-diameter of 0.22 This fraction corresponds to the axenic supernatant (cell-free) 1× (undiluted) which was kept frozen at −20° C. until later use.

II. Concentration of sample components: The 1× Supernatant was concentrated 10 times by lyophilisation and then an additional 4× by adding PEG to the sample and dialysing overnight at 4° C. with a membrane of 12 kDa cut-off at 4 (ON).

III. Removing majority pollutants: This part was performed in two steps.

(a) ultrafiltration by using a membrane of 10 kDa cut-off: the volume of the concentrated supernatant was reduced 10 times (in total 400×), maintaining the inducing activity retained by the membrane (molecular weight greater than 10 kDa);

b) Anion exchange chromatography: the retained solution with major activity was thereafter fractioned using a FPLC system (Pharmacia), and a column packed with Q Sepharose Fast Flow matrix (Q) (Pharmacia-FPLC) balanced in Tris-HCl buffer pH 7.5 and eluted by increasing ionic strength: discontinuous increasing NaCl gradient at concentrations of 0.24M (8 min), 0.38M (8 min) and 1M (10 min). Eluted fractions were collected together in 4 protein pools which were phytopathologically assayed (FIG. 3). The defense elicitating activity was found to be concentrated in peak I.

Plant pre-treatment with the Q column flow-through at pH 7.5 produces full protection against virulent isolate M11, while high—though not total—protection is achieved with protein pool II which weakly interact with the matrix (eluted with 0.24M NaCl).

These results lead to conclude that the liquid culture supernatant of avirulent isolate *Acremonium strictum* SS71 of the invention contains two or more proteins having inducing defense activity, proteins presenting different pI. However, since the maximum induction activity of resistance to anthracnose is obtained from the portion of proteins that do not interact with the anionic exchange matrix Q at pH 7.5, this basic protein pool (pI>8) was selected to continue the purification.

Figure 4:
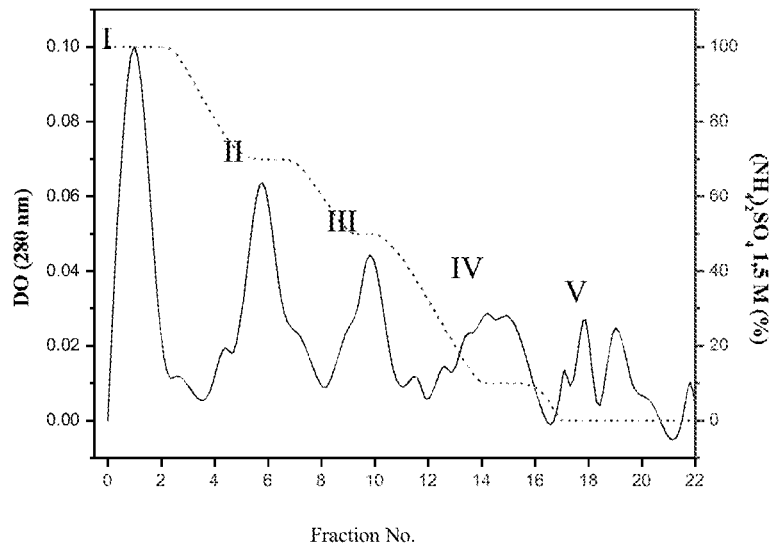
FIG. 4.

IV. Removing very closely related trace pollutants ("Polishing"):

Proteins unbound to the Q matrix (pool I) were separated by chromatography through a Hydrophobic Interaction matrix. For such purpose, pool I was cultured, under high ionic strength conditions, in a Phenyl Superose HP (PS) hydrophobic interaction column adapted to a FPLC system. The matrix was previously balanced with Tris HCl buffer 50 mM pH 7.5 adding EDTA 1 mM and $(NH_4)_2SO_4$ at 1.5M concentration, and after culturing it was eluted by decreasing the ionic strength by applying a $(NH_4)_2SO_4$ decreasing concentration gradient, thereby obtaining the profile shown in FIG. 4. The elicitor inducing activity was found to be concentrated in peak IV.

Figure 5:
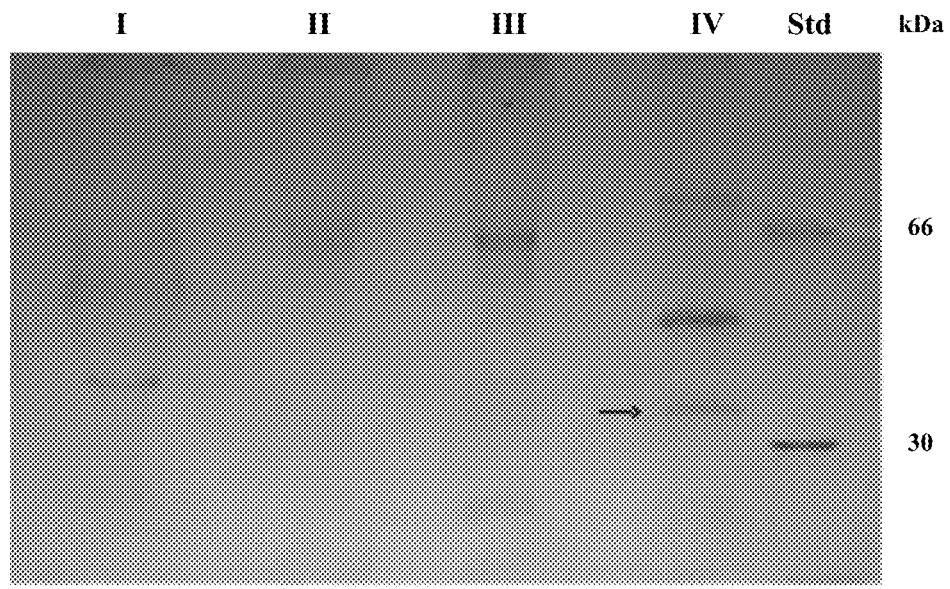
FIG. 5.

When proteins unbound to the Q matrix were run through a PS matrix, protection activity was found to be divided among three fractions eluted by decreasing the ionic strength: pools II, III and IV, which upon observation in a 12% polyacrylamide gel did not contain single protein bands (FIG. 5). The main activity is concentrated in peak IV. A new chromatographical separation was performed using the same system (matrix and buffers), but applying a $(NH_4)_2SO_4$ discontinuous gradient having 5 intermediate steps. Using this procedure 10 chromatographical peaks were obtained, which contained single proteins as observed by single bands in SDS-PAGE (10%) dyed with Coomassie Blue-R. Defense elicitor activity detection was carried out spraying one leaf in plants (n=4) with each of the obtained fractions conditioned to a concentration of 2.5 μg protein/ml. Results showed that peak 7 which is eluted with $(NH_4)_2SO_4$ at 0.5 M concentration, provides plants with full protection against anthracnose ($DSR_{40}$=1) and also induces ROS production (NBT and DAB positive dyes).

Figure 6:
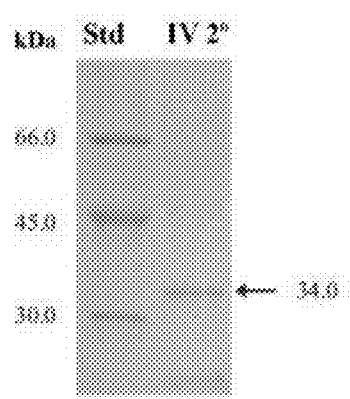
FIG. 6.
Figure 7:
FIG. 7.

As shown in FIG. 6, when peak 7 is separated by SDS-PAGE at 10% a single band is intensely coloured with Coomassie Blue-R. The active protein elutes from the column with 0.5 M of $(NH_4)_2SO_4$.

A 34 kDa basic protein was purified to homogeneity, which is capable of inducing systemic resistance against the attack by virulent isolate M11 of *C. acutatum*.

The elicitor polypeptide is a new protein, different from other previously reported proteases. To confirm this, even though no accessions of protein sequences described in *Acremonium* spp. were registered among the top 100 hits obtained by Blast-P performed with the elicitor protein sequence, the identity degree thereof was studied with all the proteins that have been reported as proteases or protease-like in this genus.

Table 1 summarizes the characteristics of amino acid sequences of *Acremonium* genus proteins (producing organism, source, extension, Mr, number of amino acids and function) and the comparison thereof with the elicitor protein (percentages of identical amino acids and gaps obtained from alignment with each of them).

In all genomic and proteomic databases, only 6 protease-like protein sequences produced by different species of *Acremonium* spp. have been reported. Two which were determined on an experimental basis and correspond to amino terminal sequences partial sequence) with proved proteolytic function (No. Acc. P85156, Sub-E1 of 40 a.a.) (No. Acc. P85157, Sub-E2 of 18 a.a.), while the remaining four are sequences inferred by homology from genomic DNA depositions. Among these later sequences, an internal protease fragment (No. Acc. AAC09289.1, Pr.) and three full length sequences corresponding to a subtilisin-like serine protease (No. Acc. BAF62454.1; Sub-E3), an alkali proteinase precursor (No. Acc. BAA00765.1; Pr.A1c) and a cephalosporine C acetilhydrolase (No. Acc. CAB87194.1; AcH) are described.

TABLE 1

Description of protease-like proteins of Acremonium spp. recorded in protein databases (Uniprot).

| | *Acremonium* spp. proteins described | | | | | | Comparison to elicitor | |
|---|---|---|---|---|---|---|---|---|
| Accession No. | Description | Organism | Protein Existance | Function | $M_r$ Extension | Abbrev | Ident. (%) | Gaps (%) |
| P85156 (ASE1_ACRSP) | Subtilisin-like serine protease AS-E1 | *Acremonium* sp. | Experimental evidence | Prothrombine and fibrinogen cleavage, and plasma clotting inhibition. | Amine terminus 40 aa 4.327 kDa | Sub-E2 | 72.50 (29/40) | 0 (0/40) |
| P85157 (ASE2_ACRSP) | Subtilisin-like serine protease AS-E2 | *Acremonium* sp. | Experimental evidence | Prothrombine and fibrinogen cleavage, and plasma clotting inhibition. | Amine terminus 18 aa 1.914 kDa | Sub-E1 | 61.11 (11/18) | 0 (0/18) |
| AAC09289.1 | Protese P1 | *Acremonium coenophialum* | Inferred by homology (genomic DNA) | | Internal fragment 92 aa | Pr. | 59.78 (55/92) | 0 (0/92) |
| BAE62454.1 | Subtilisin-like serine protease | *Acremonium* sp. (F11177) | Predicted (genomic DNA) | Prothrombine cleavage | Full 535 aa 58.371 kDa | Sub-E3 | 39.17 (152/388) | 13.78 (62/450) |
| BAA00765.1 | Alkali protease precursor | *Acremonium chrysogenum* | Inferred by homology (genomic DNA) | | Full 402 aa 42.099 kDa | Pr.Alc | 44.8 (168/375) | 9.42 (39/414) |

TABLE 1-continued

Description of protease-like proteins of Acremonium spp. recorded in protein databases (Uniprot).

| Accession No. | Acremonium spp. proteins described | | | | | | Comparison to elicitor | |
|---|---|---|---|---|---|---|---|---|
| | Description | Organism | Protein Existance | Function | $M_r$ Extension | Abbrev | Ident. (%) | Gaps (%) |
| CAB87194.1 | cephalosporine C acetilhydrolase | *Acremonium chrysogenum* | Inferred by homology (genomic DNA) | Non-specific esterase. Deletion of cephalosporine C acetyl group | Full 383 aa 38.223 kDa | AcH | 53.68 (204/280) | 2.06 (8/388) |

Figure 8:
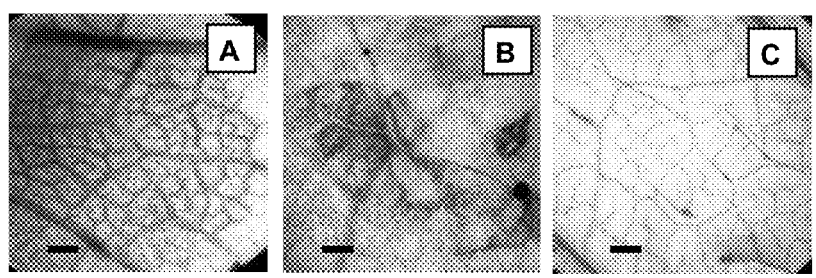
FIG. 8.

As shown in Table 1, elicitor protein alignments with Sub-E1, Sub-E2 and Pr fragments result in high identity values ranging between around 59.8 and 72.5% without breaking gaps in the sequence alignments. However, the short amino acid sequence (40 to 92 aa) of these proteins prevent any homology inference with the elicitor protein, since more than 75% of their sequence is unknown.

On the other hand, in relation to the full length proteases reported in *Acremonium* spp., the elicitor protein shows 39.2% of identity with Sub-E3 and 44.8% of identity with the Pr.A1c alkali protease; however, in both alignments very high gap percentages are obtained (13.8% and 9.4%, respectively). Sub-E3 is the only full length sequence subtilisin-like serine protease described in *Acremonium* spp. which in addition presents experimentally proven proteolytic activity (Liu et al., 2007). Nevertheless, this protease presents a very low similarity percentage (39.2%) as compared to the defense-inducing subtilisin isolated from *A. strictum.*

Surprisingly, the highest identity value (53.7% of identity and 2.1% of gaps) of the elicitor protein corresponds to the protein AcH of *A. Chrysogenum*. It is a non-specific esterase, which acts by eliminating the antibiotic cephalosporine C acetyl group. Even though it lacks proteolytic activity, AcH was included in the analysis because of its sequence similarity to serine proteases.

The following comparison shows an alignment performed with the amino terminal sequences of all proteases reported in *Acremonium* spp., including the elicitor protein, showing the variability of the amino terminal region between these proteases.

| | | | |
|---|---|---|---|
| (SEQ ID NO: 21) | Elicitor | 106 | YTASTRPGTAQ |
| (SEQ ID NO: 22) | AcH | 105 | IQAESQEPGTAD |
| (SEQ ID NO: 23) | Sub-E1 | 1 | DVTTAEY |
| (SEQ ID NO: 24) | Sub-E3 | 146 | DSELEKATLSFA TFNKAAEEVDATN |
| (SEQ ID NO: 25) | Pr. Alc. | 120 | ALVTQATPSSYAL |
| (SEQ ID NO: 26) | Sub-E2 | 1 | YVSG |

The assays performed to determine the elicitor activity are shown in FIG. 7. The plants treated with the elicitor exhibit the same general status as the Cross-Protection control plants, and are completely healthy plants ($DSR_{40}$=1) of great size. It was also verified that fractions derived from the avirulent pathogen isolate SS71 of *A. strictum* of the invention do not present any type of virulence against a *Fragaria vesca* (wild strawberry) genotype which is highly susceptible to this type of fungal pathogens. These results are consistent with the possibility of using these fractions to confer field protection against anthracnose in cultured strawberry (*F.×ananassa*) cv. Pajaro.

The protocol and experimental design used to assess the induction of resistance against anthracnose by the different purification fractions obtained are detailed in Table 2 (see examples).

The defense response induced by fractions of the avirulent pathogen and by the polypeptide having elicitory activity of the present invention in strawberries has been characterized.

The events associated with the plant defense produced by the polypeptide of the invention derived from the avirulent pathogen isolate SS71 of *A. strictum* were analyzed.

Defense reactions were assessed in strawberry plant leaves of the Pajaro cultivar treated with active pre-purified extracts derived from isolate SS71 cultures of the invention, and such results were subsequently confirmed with the pure inducing protein. In these assessments, accumulation of reactive oxygen species ($H_2O_2$ and $O_2$) associated with the oxidative burst; nitric oxide (NO) production; accumulation of phenolic compounds; microscopic hypersensitive response (micro-HR); reinforcement of cell wall by lignification and by callose deposition; accumulation of salicylic acid and expression of genes associated with the defense response and the systemic acquired resistance (SAR) e.g. PR-proteins, were observed. The aforementioned indicate that general induced plant defense is obtained, found in all plant species studied as of today. Some of these responses were studied and found in other plant species after application of the subtilisin protein isolated from *A. strictum* (tomato and *Arabidopsis*). It can be concluded from these experiments that there is a general effect in different cultures against fungal and bacterial pathogens, which is also grounded by positive resistance results against *Colletotrichum* spp. (biotrophic fungus), *Botrytis cinerea* (necrotrophic fungus) and *Xanthomonas fragariae* (bacteria). As mentioned above, the response against the elicitor of the invention includes accumulation of salicylic acid, which induces resistance not only against fungal and bacterial pathogens but also against viruses. Consequently, the present invention is also useful to induce resistance against viruses in plants. The oxidative burst was assessed by the accumulation of ROS. It was analyzed whether the protective effect observed in plants pre-treated with the elicitor was preceded by biochemical markers usually associated to the defense, and also the accumulation of superoxide ion radical ($O_2.^-$) and hydrogen peroxide ($H_2O_2$) by histochemical dyeing with NBT (nitroblue tetrazolium) and DAB (diaminobenzidine), respectively.

The production of $H_2O_2$ (DAB+) and $O_2.^-$ ion (NBT+) was observed in application areas 2 hours after treatment (hpt) with the elicitor. Both, proximal leaflets as well as distal leaves (non-treated) were analyzed. Maximum production was observed for both ROS species 4 hpt, as shown in FIG. 8A for $H_2O_2$ and FIG. 8B for $O_2.^-$ ion. However, the superoxide ion detection became almost histochemically neglectable at later time points, while hydrogen peroxide levels continued at a high detection level 12 hpt. In contrast, no production of any reactive oxygen species was observed in control plants treated with either PG medium or water (FIG. 8C).

When pure protein was infiltrated through the abaxial side of a plant leaflet, ROS production was observed (DAB+ and NBT+ dyes) in discrete micro sites, uniformly distributed throughout the surface of the infiltrated leaf (proximal tissue) and unfiltered leaves (distal tissue) known as systemic microoxidative bursts.

Figure 9:
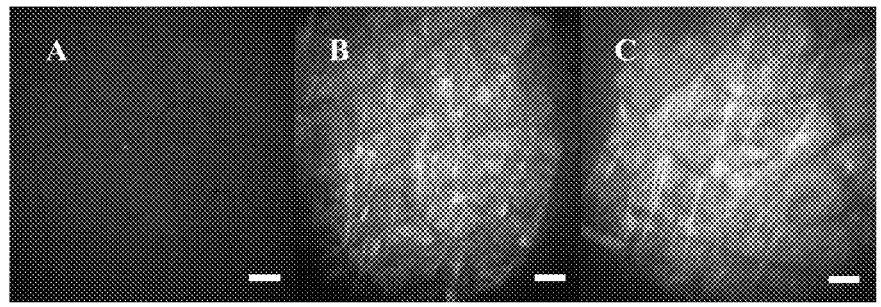
FIG. 9.

The accumulation of self-fluorescent compounds was assessed. Results shown in FIG. 9 demonstrate that leaves infiltrated with active extracts or the pure protein exhibit a strong self-fluorescent signal at 329 nm observed under UV light at the infiltration point, which is accompanied by a tissue necrotic lesion, whereas leaves infiltrated with water (control) do not present detectable self-fluorescence or tissue necrosis. The self-fluorescence assessment was carried out at the infiltration point at different times after induction. At 12 hpt (hours post-treatment) under UV light the apparent presence of a yellow self-fluorescence was observed (FIG. 9B), with gradual increased intensity, reaching its maximum point 72 hpt (FIG. 9C). At the infiltration point of control plants, no self-fluorescence is observed (FIG. 9A). Yellow self-fluorescence is probably due to the release of phenolic compounds derived from the phenylpropanoid route (i.e. phytoalexines), which is strongly activated during HR.

Figure 10:
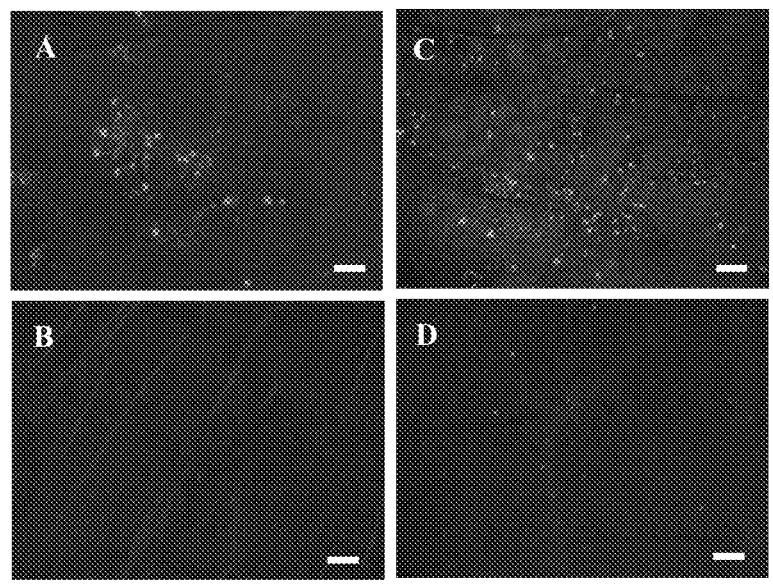
FIG. 10.

Changes in cell wall composition induced by the defense response were also analyzed, by assessing deposition of callose. For this purpose, water (control), cell extracts with defense-inducing activity and purified subtilisin protein were analyzed for capacity to induce accumulation of callose in strawberry plant cell walls. FIG. 10 shows plants accumulating callose 7 days after treatment with the pure elicitor protein from strain SS71 (FIG. 10B), whereas no accumulation is detected in plants treated with water (FIG. 10A). However, FIG. 10 also shows that callose is deposited in even higher concentrations in plants infected with the virulent isolate M11 of *C. acutatum*, in plants which had previously been induced with the elicitor 7 days prior to infection (FIG. 10C). Deposition of callose was firstly observed to occur in isolated epidermal cells and subsequently accumulating in contiguous cell groups forming a matrix acting as a sheer physical barrier to stop pathogen invasion.

Salicylic acid (SA) was quantified in phloem of strawberry plants infiltrated with pure elicitor protein at a concentration of 2.5 μg protein/ml. SA was recovered from petioles at different time points (0, 24, 48, 72 and 96 hours) aftertreatment (htp)), purified by reverse-phase chromatography and quantified by fluorescence spectroscopy excitation at 296 nm.

Figure 11:
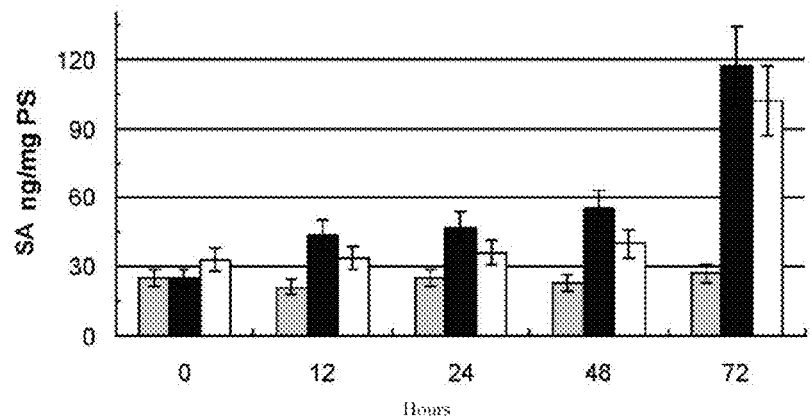
FIG. 11.

Plants treated with BTH as well as the purified subtilisin protein showed significant increase in SA concentrations in the phloem 72 hpt, reaching a concentration of 3.72 μg/ml in the phloematic exudate, while water-treated control plants presented a 2.5 times lower value (1.45 μg/ml exudate). FIG. 11 shows that plants treated with water did not present a significant increase in SA throughout the experiment, while plants treated with elicitor showed a significant increase 72 hpt, as well as BTH-treated plants (0.5 mM), used as a SAR-responsive positive control plant.

Experiments were conducted in order to determine if extracts having defense-inducing activity and the pure protein (subtilisin) were capable of translocating the defense signal and thereby inducing a SAR-like response. For this purpose, spraying of a single plant leaf was performed with the pure protein (5 μg protein/ml), and after 7 days (7 dpt), the rest of the plant was infected with a conidial suspension of virulent isolate M11. BTH and SA were used as SAR-inducing positive controls, while a negative plant control was obtained by spraying with water.

Figure 12:
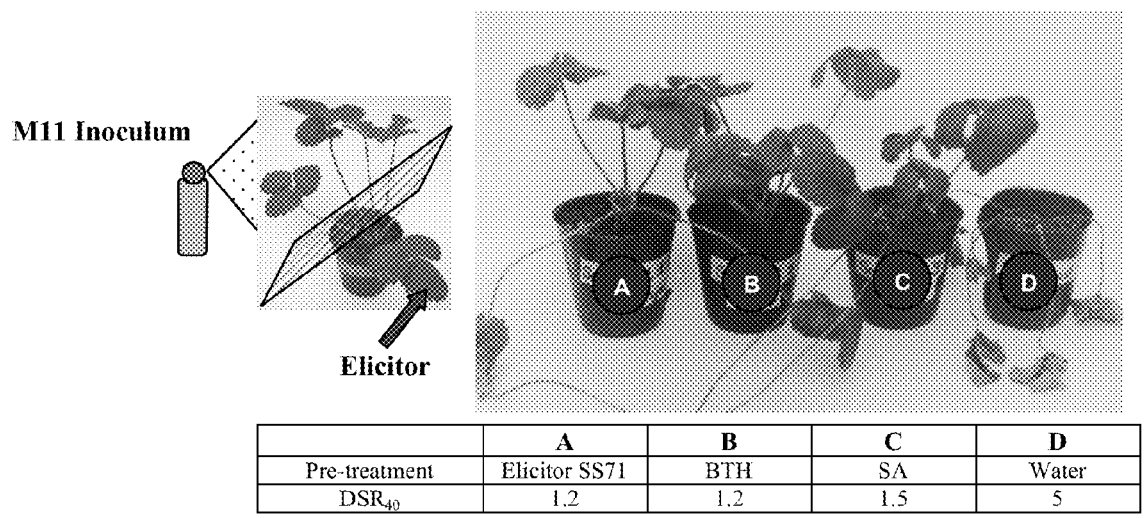
FIG. 12.

As shown in the table appended to FIG. 12, plants pretreated by spraying a single leaf with the elicitor of the present invention present a DSR lower than 1.5 as of 40 days post-inoculation, as well was plants treated with BTH and SA, while plants pre-treated with water die 10 dpi (DSR=5). This confirms that the elicitor provides plants with a systemic-like protection, since plants where only one leaf had been treated didn't exhibit disease symptoms.

In order to investigate the resistance-inducing action of the elicitor polypeptide of the present invention a defense assay was performed in other strawberry cultivars and in different plant species. The pure elicitor derived from isolate SS71 of the invention provides protection to different strawberry cultivars when challenged with virulent strains of *C. acutatum*.

Different commercial varieties of strawberry presenting either an incompatible-like interaction (e.g. cvs. Pajaro and Camarosa) or a compatible-like interaction (e.g. cvs. Milsei Tudla, and Chandler) were tested for pathogen defense-induction after treatment with the elicitor from SS71. After treatment with the inducer, all plants were challenged with a virulent strain for each cultivar, *C. acutatum* M11 (isolate of cv. Chandler in Manantial-Tucuman), MP3 (isolate of Aroma plants in Mar del Plata) or LCF 1-05 (isolate from fruits of Camarosa Lules-Tucumán).

Figure 13:
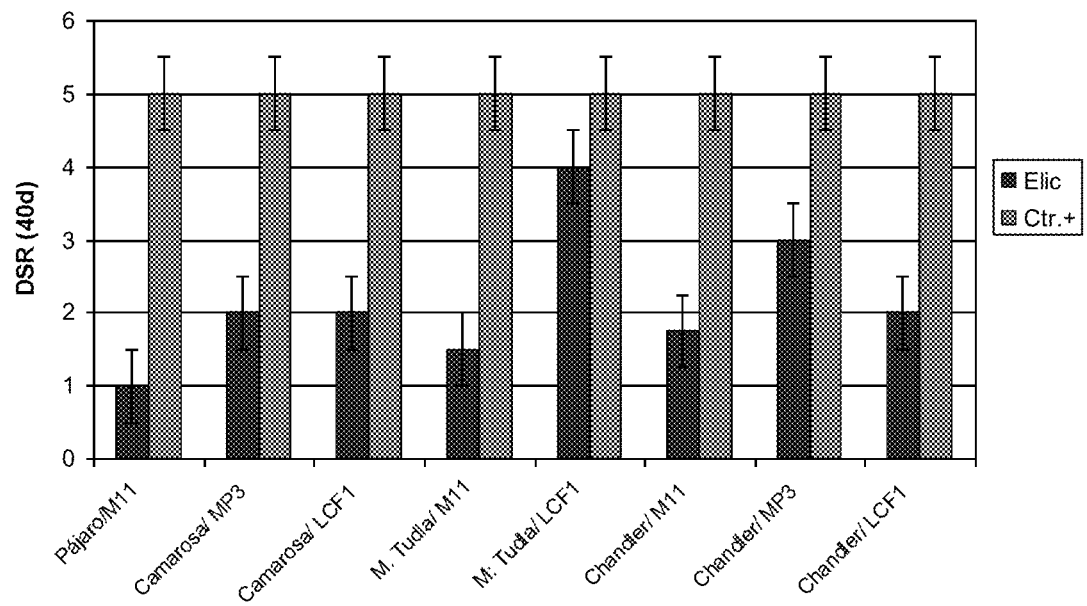
FIG. 13.

FIG. 13 shows that after treatment with the elicitor, cvs. Pajaro and Camarosa do not present disease symptoms (DSR=1) as of 40 dpi, while cvs. M. Tudla and Chandler plants presented different degrees of disease development, depending on the isolate used for infection. These results demonstrate that in general, all varieties exhibit lower disease symptom values than control plants, and in most cases showed a remarkable recovery 30 dpi (DSR=1-2).

The elicitor derived from SS71 develops high efficiency protection against anthracnose in SS71-resistant cvs. (wherein it behaves on an avirulent basis), while leading to partial protection in SS71-susceptible cultivars (wherein it behaves on a virulent basis).

FIG. 13 also shows that the protection degree particularly depends on the isolate being used. While the elicitor can rapidly control the infection caused by M11 in all the cultivars analyzed, the disease protection differs with isolates MP3 and LCF1.

These results conclude that the elicitor of the invention has a broad-spectrum inducing activity since it is capable of inducing defense responses in other cultivars and against other pathogens, though at different protection degrees.

Figure 14:
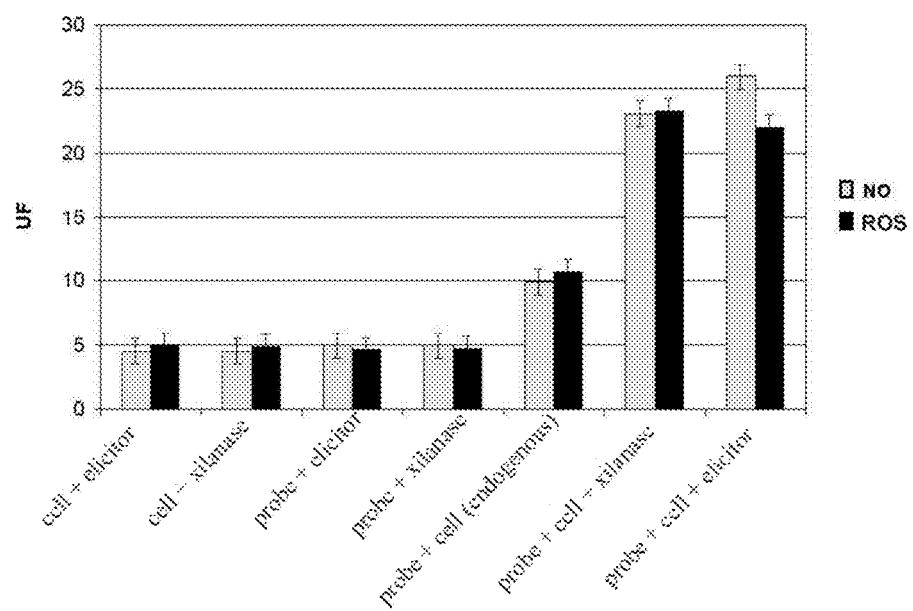
FIG. 14.

The induction of reactions associated to defense in other plant species was studied. For example, the effect of the elicitor on a tomato cell culture (*Lycospersicum solanum*) was investigated, analyzing if the elicitor is capable of inducing the accumulation of ROS and NO (nitric oxide) as biochemical markers of the plant defense. Purified protein (subtilisin) was added at a final concentration of 5 μg/ml or 10 μg/ml to cell cultures to assess ROS or NO evolution, respectively, by fluorescence measurements. FIG. 14 shows that while tomato cells exhibit strong and rapid ROS and NO accumulation, during the first 30 minutes after adding the elicitor. Control cells did not exhibit any ROS or NO accumulation above baseline levels.

Figure 15:
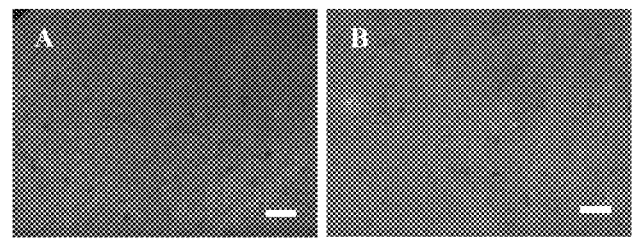
FIG. 15.

In addition, the elicitor capacity to induce ROS production in *Arabidopsis thaliana*-plants was studied. For this purpose, hydrogen peroxide production and superoxide radical production were studied in parallel. Intracellular hydrogen peroxide was assessed with a Dichlorofluorescin diacetate (DCFH-DA) fluorescent probe, observing a peak of burst as a consequence of the treatment with the pure elicitor protein. This result confirms the capacity of the protein of the invention to induce hydrogen peroxide intracellular accumulation, despite the fact that the accumulation peak does not correspond exactly to the time point to that observed for strawberries wherein the maximum peak is produced 4 hpt (FIG. 15).

Figure 16:
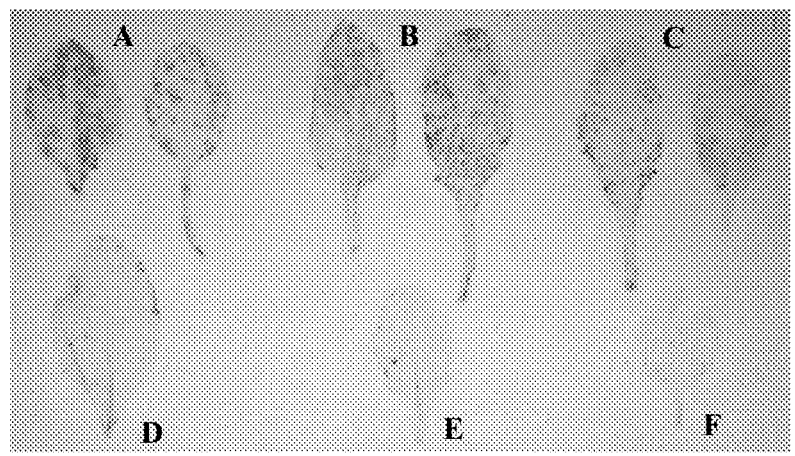
FIG. 16.

The accumulation of superoxide radical in leaves of *A. thaliana* was assessed with NBT (see above), observing an accumulation peak 4 hpt, coinciding with the generation of superoxide in strawberries, while control leaves did not present any reaction (FIG. 16).

In order to provide a chemical and molecular characterization of the resistance inducing activity polypeptide of the present invention, the molecular weight of this protein was determined by 10% SDS-PAGE (with β-mercaptoethanol using the PD Quest software (BioRad), giving an approximate value of 34 kDa. The polypeptide presents a pI of around 9.5 determined on an experimental basis by isoelectric focusing electrophoresis.

The NH$_2$-terminal sequence of the previously reduced and alquilated protein transferred to a PVDF membrane, as well as three-internal-peptide sequences obtained by in gel tryptic digestion of the reduced and alquilated protein, were obtained. FIG. 17 shows the peptide sequences with 1095.19, 2441.2 and 1938.1 MS/MS molecular mass. Alignment analysis showed that all peptide sequences have, each individually, high similarity with fungal proteases from the subtilisin family. The highest sequence identity values correspond to a subtilisin from *Arthroderma* spp. (or *Trichophyton* spp.) for the peptide with a molecular mass of 2441.2 and a subtilisin protein from *Aspergillus* spp. for the peptide with a molecular mass of 1938.1.

Figure 18B:
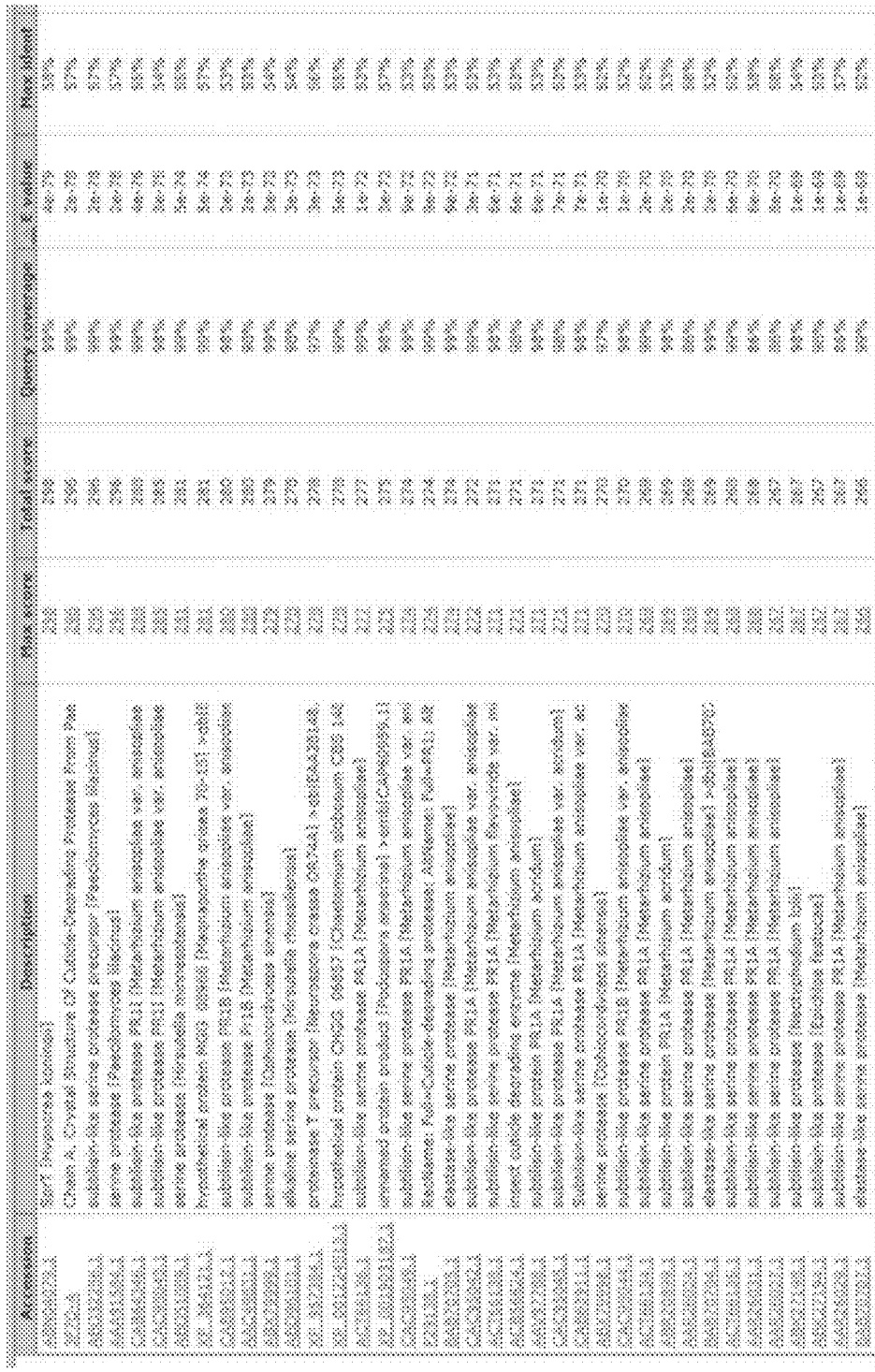
FIG. 18.

Oligonucletide primers were designed from the peptide fragment sequence shown in FIG. 17, knowing that the first peptide corresponds to the protein amino-terminal end. The corresponding cDNA sequence was obtained by an amplification protocol corresponding to the entire mature elicitor protein transcript and the deduced nucleotide sequence thereof is shown in FIG. 18A. Having access to the entire cDNA sequence of the elicitor, the similarity of this sequence was compared against sequences in the protein and DNA sequence databases, in order to obtain information on protein function and belonging to protein family. From this study it was concluded that the isolated sequence is actually a serine protease of the subtilisin family.

Figure 19B:
FIG. 19: (A): Elicitor protein sequence derived from cDNA nucleotide sequence (SEQ ID NO: 2) is shown; (B): Amino acid sequences producing maximum similarity values and source species obtained by Blast P; (C): structure of a subtilisin obtained from Trichoderma koningii indicating 19 inhibitor domain and S8 catalytic domain. It is shown that the obtained sequences that are fragments of the invention (34 kDa plant defense elicitor protein) are within the protein catalytic domain (peptidase S8). Each domain amino acid length is also shown.
Figure 19:
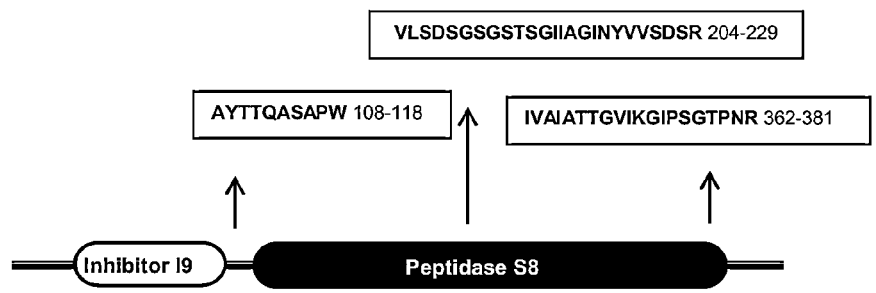

In order to complete the study and confirm the result, this protein affiliation was also studied by Blast P. For such purpose, the amino acid sequence deducted from the nucleotide sequence shown in FIG. 18 was used, thereby obtaining the sequence shown in FIG. 19A. This analysis confirmed that the isolated sequence corresponds to a serine protease of the subtilisin family (FIG. 19B).

In order to gain a better overview of the relative positions of domains having higher similarity, a complete sequence comparison between the *A. strictum* subtilisin amino acid sequence with sequences belonging to the subtilisin family was performed. For such purpose, subtilisin from *Trichoderma koningii*, *Metarhizium anisopliae* var. *anisopliae*, *Ophiocordyceps sinensis*, *Paecilomyces lilacinus* were selected because of having both high nucleotide (Blast X) and amino acid (Blast P) sequence identity. The structure of the subtilisin of *Trichoderma koningii* was taken as model since it has high sequence identity with the elicitor subtilisin of *A. strictum*. FIG. 19C shows the relative position of the sequenced fragments from the elicitor of *A. strictum* in relation to the characterized domains of the subtilisin of *T. koningii*. The results shown let us conclude that the amino-terminal end is located in the region located between the Inhibitor 19 domain and the Peptidase S8 domain having protease function, while the other two sequenced internal peptide sequences are located in the Peptidase S8 domain. The peptidase 19 inhibitor domain was found in the immature form of all referenced subtilisins analyzed.

These results suggest that the immature elicitor protein experiences post-translational maturation, consisting in the cleavage of the inhibitor 19 domain, which can be the signal propeptide for export to the extracellular medium. Based on the results shown above, we know that that sequences are highly conserved in the domain having protease function, therefore we can infer that such proteins show proteolytic activity.

Figure 20:
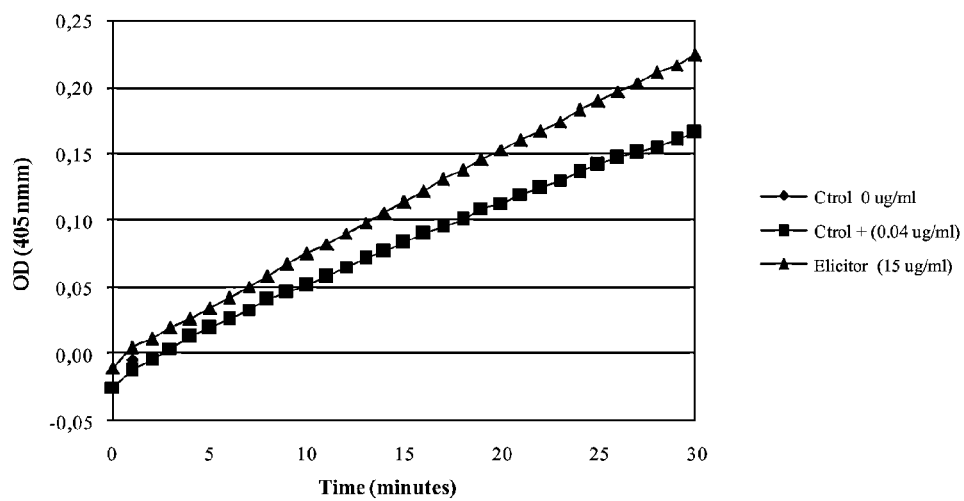
FIG. 20.

In order to experimental determine whether the subtilisin-like elicitor protein has a proteolytic function, the capacity thereof was studied using a specific chromogenic substrate (N-Succinyl-Ala-Ala-Pro-Phe p-Nitroanilide) releasing p-NA which absorbs at 405 nm when proteolyically cleaved. FIG. 20 demonstrates that the elicitor protein (15 µg/ml) acts on the chromogenic substrate producing the proteolysis thereof over time, as well as the subtilisin of *Bacillus subtilis* (0.04 µg/ml) used as positive control.

After being purified to homogeneity, the elicitor protein exhibits proteolytic activity on the subtilisin specific chromogenic substrate, i.e., it has in vitro subtilisin-like protease function.

This invention is better illustrated according to the following examples, which are not to be construed as a limitation on the scope thereof. In contrast, it should be clearly understood that other embodiments, modifications and equivalents thereof can be applied, which upon reading the present specification can be suggested by those skilled in the art without departing from the spirit of the present invention and/or scope of the appended claims.

EXAMPLES

Example 1

Materials and Media Used Strawberry Plants

*Fragaria×ananassa* Duchesne cultivar Pajaro strawberry plants and wild strawberry *Fragaria vesca* specie were used; all available at Pro/Frutilla germplasm bank.

The material was produced in three stages: (1) Meristem in vitro culture; (2) Rustication; and 3) Stolon plant multiplication.

(1) By meristem in vitro culture, plant material was cleaned and multiplied under axenic and controlled growth conditions (temperature: 25° C.—photoperiod: 16 h of light). (2) Then, it was rusticated in trays using a mixture of earth and perlite as a sterile substrate (2:1). After four weeks, plants were transplanted to plastic pots, 8 cm height×8.5 cm diameter, thereby obtaining mother seedlings. (3) These mother seedlings were grown in growth chambers under controlled temperature (25-27° C.), humidity (70%) and photoperiod (16 h), conditions being optimal for stolonization. All plants used for experimental procedures were obtained by fixation of mother seedling stolons (asexual propagation) in sterile substrate under axenic conditions and then further grown under the same growth conditions. Once rooted, around two weeks later, new seedlings were separated from the mother plant and set to grow for another 12-14 weeks. That is, mother seedlings are grown up to they are overall 14 to 16 weeks old, having at least four fully expanded leaves, representing a relatively early growth stage for the seedling. During this period, seedlings were watered only with destilled water twice a week and did not receive preventive application of fungicides or fertilizers.

A. strictum SS71/C. acutatum M11 cross-protection system response was assessed in cultivar Pajaro, wherein it was defined and characterized.

An ecotype from *Fragaria vesca* wild strawberry was used in all the assays as a strain virulence positive control because of its extreme susceptibility to the strain SS71 of *A. strictum*. This genotype was also used as inactivation control for *A. strictum* SS71 in the fractions derived from such strain to demonstrate that they do not produce any disease, which serves for substantiating the applicability of this biocontrol methodology in the field.

*Arabidopsis* Plants

*Arabidopsis thaliana* wild type (ecotype Columbia) seeds were germinated on MS medium (½ diluted) supplemented with 1% sucrose and 0.8% agar. When having two leaves, seedlings were transplanted to a sterile substrate, and were kept in growth chambers under optimal growing conditions (22° C., 70% humidity, 12 h of light) until 4 weeks old.

Cell Cultures in Suspension

Cells cultured in suspension (*Solanum lycopersicon* cv. Money Maker; line Msk8) were grown at 24° C. in the dark at 125 rpm in MS medium (Duchefa, Haarlem, The Netherlands) supplemented with NAA 5.4 μM, 6-benzyladenine 1 μM and vitamines (Duchefa) as described previously (Felix et al., 1991. Plant Physiol. 97, 19-25).

Fungi:

The following strains were used: SS71 of *Acremonium strictum* of the invention and strain M11 of *Colletotrichum acutatum* for infection. These strains were used in the *A. strictum/C. acutatum* cross-protection system defined in cv. Pajaro. In this system, strain SS71 produces the compound with defense elicitory activity, and strain M11 is the virulent strain against cv. Pajaro used for the assessment of the inducing activity exhibited by the increased resistance to anthracnose (produced by M11) in plants previously treated with strain SS71.

To study the protecting elicitory activity against anthracnose in other strawberry cultivars, other strains of *Colletotrichum acutatum* (e.g. MP3, LCF1) were used, having virulent behaviour against the respective cultivars.

Culture Media

Avirulent pathogen strains of *A. strictum* of the invention were cultured in agar-potatoe-glucose medium with 1.5% agar (APG 1.5%). After being melt, the medium is cooled to 45-50° C. and distributed in sterile Petri plates (15 ml per box), after adding Streptomycine Sulphate (Richet) to a final concentration of 300 μg/ml. The liquid culture of the strain SS71 of *A. strictum* was carried out in potatoe-glucose (PG) medium which exhibits equal composition as the APG medium without adding agar and is obtained by the identical procedure.

Culture Conditions

Strains were kept in conidial suspensions ($10^7$-$10^8$ conidia/ml) in 50% glycerol and kept frozen at −70° C.

Solid Cultures

Cultures of the different strains in solid medium were obtained by seeding mycelium on APG 1.5% medium or by seeding conidia kept in glycerol, and then incubation for 10 days under optimal growth (28° C.) and esporulation (continuous white light) conditions.

Liquid Cultures

Cultures in liquid medium for the strain of *A. strictum* of the invention were obtained inoculating 40 ml of (PG) culture medium, contained in 100 ml capacity glass containers, with such volume of aqueous conidial suspension to obtain a final concentration of $10^6$ conidia/ml culture medium. The conidial suspension was prepared on the assay day from a new plate culture (see "Conidial Suspension Preparation" below). Then, the inoculated liquid medium was incubated under optimal and favourable conditions for sporulation, i.e. 28° C. with continuous white light and without stirring up to stationary growing phase (21 days). This culture was called SN.

Cultures were followed by macroscopic and microscopic observations. Macroscopic observation is qualitative, observing: formation of mycelial film on top, colour, turbidity or opacity, compaction degree and solidity. Microscopic observations consisted in observing at 40× magnification, a wet preparation (between slide and cover slip) to assess culture purity and uniformity and the lack of spurious cells indicating any contamination.

Example 2

Conidial Suspension Preparation

The suspension was prepared under sterile conditions from new cultures of strain *A. strictum* SS71 or M11, grown on APG medium at 1.5%. Conidia were collected scratching the colony surface with a sterile loop or spatula. Then, conidia were resuspended in a certain volume of sterile distilled water (5 or 15 ml). Conidia were mixed by vortex for 1 minute and filtered through some lint with a sterile syringe. Conidia were counted in a Neubauer chamber and then depending on the use intended for the suspension, two different procedures were performed.

As for assays wherein the live conidial suspension of strain SS71 of *A. strictum* or M11 of *C. acutatum* was used to inoculate the plants, the suspension was adjusted by dilution with sterile distilled water, to a conidial concentration of $1.5\times10^6$ conidia/ml. Finally, Tween 20 was added to the suspension at 0.1% v/v final concentration, as a tensioactive agent.

As for inoculation assays wherein the strain SS71 of *A. strictum* was used inactivated (see "Phytopathological Assays" below), the avirulent pathogen conidia were inactivated before the dilution performed to adjust the concentration to the desired value. In these cases Tween 20 was not used so as to avoid a possible interaction between this tensioactive agent and the active compound.

Example 3

Method for Obtaining the Conidial Extract (CE)

The concentrated conidial suspension of avirulent *Acremonium strictum* SS71 of the invention (at $10^8$ conidia/ml concentration) was fractioned in 1.5 ml aliquots in 2 ml tubes. Each aliquot was treated by ultrasound until the typical opalescence of the suspension disappeared, obtaining a translucent liquid. For such purpose, the suspension was subjected to sonication for 15 minutes, with intermittent pulses (each sonication cycle was 20 seconds long, separated by 10 seconds rest periods) at 60% intensity and 40 W power in ice bath. Brandon Sonifier Tune 40 titanium-tip equipment was used. The tube containing the conidial suspension was kept in an ice bath (0-4° C.) to avoid overheating.

After sonicating the sample, a wet preparation was subjected to microscopic observation (40×) to determine the conidial destruction degree as compared to the starting concentration, so as to estimate cell lysis efficiency by the sonication method. Then, the sonication product was filtered through a membrane (Millipore GV in PVDF) 0.45 μm pore-diameter, so as to remove cell remains and conidia not destroyed during the treatment. Protein concentration was also determined, giving values around 1.5 μg protein/ml. The treated suspension was then diluted by sterile distilled water to reach a concentration equivalent to $1.5 \times 10^6$ conidia/ml based on the starting conidia count, amounting to 0.12 μg protein/ml final concentration. This fraction is herein referred to as CE.

Suspension volumes and sonication times and cycles were standardized in order to optimize cell lysis.

Example 4

Obtaining the Liquid Culture Supernatant (SN)

The starting cultures were two equal liquid cultures (PG medium) of *A. strictum* SS71, 40 ml each, which were inoculated and incubated and explained above. Upon completing the growing stage, each culture was centrifuged at 10,400 g for 20 min at 4° C., removing the pellet and recovering the supernatant. Then, the supernatants of both cultures were collected and centrifuged again at 10,400 g for 30 minutes at 4° C. the residual sediment. Subsequently, the recovered supernatant was subjected to subsequent filtrations under sterile conditions to remove resuspended conidia. First it was filtered through a Whatman No. 2 filter paper, then by Millipore cellulose nitrate membrane filter 0.8 μm pore-diameter and finally by Millipore cellulose nitrate membrane filter 0.45 μm pore-diameter. The axenic filtrate is the cell-free liquid culture supernatant (SN). In this case, a 25 ml volume was recovered, which was determined to have 8.43 μg de protein/ml protein concentration.

The two culture fractions of *A. strictum* SS71, both the cell-free extract (CE) and the liquid culture supernatant (SN) were subjected to a sterile control consisting in striation of the filtrated product in 1.5% APG sterile fresh medium followed by plate incubation for 48 h at 28° C. and under continuous white light. The absence of fungal growth confirmed the absence of viable cells in the filtrate, either vegetative cells in the extracts or reproductive structures (conidia) in the filtrates.

Example 5

Characterization of the elicitor present in the SN produced from *Acremonium strictum* of the invention.

Thermal Stability Determination

To determine the active compound thermal stability two thermal treatments of different severity were used. For such purpose, a volume of 25 ml SS71 liquid culture cell-free supernatant, which retains the capacity to provide protection against the stain of *C. acutatum* causing anthracnose, was subjected to:

A—Heating by boiling in a water bath (100-95° C. for 15 min, at atmospheric pressure) (Product SN1).

B—Autoclaved (121° C. for 15 min at overpressure 1 atm) (Product SN2).

The protein content in the samples corresponding to both treatments was below the detection limit of the method employed.

C—Proteolysis with Proteinase K (SIGMA): to a solution containing elicitory activity (10 μg protein/ml) the enzyme was added at 100 μg proteinase/ml final concentration and it was incubated at 50° C. for 1 hour (this extract is referred to as SNA) or overnight (12 h, this extract was referred to as SNB).

The products obtained after each inactivation treatment (CE and SN products and derivatives thereof: 1, 2, A, B) were used to spray plants in the pre-treatment prior to inoculation (see "Phytopathological Assays: double-treatment system").

Example 6

Phytopathological Assays: Double-Treatment System

The experimental designed used to assess the cross-protection consists in the double-treatment strategy detailed below:

1) First Treatment: INDUCTION: it consisted in spraying the aerial parts of the plant (petioles and leaf sheets) to dripping point, with one of the fractions from the different treatments of strain SS71 of *A. strictum* (CE and SN fractions). A 5 ml volume is considered sufficient to wet the complete foliage of a 3-month-old seedling (4 fully expanded leaves).

2) Upon completion of the first treatment, plants were transferred to a monitoring chamber, where they were grown under controlled humidity (70%), temperature (28° C.) and photoperiod (16 h light) conditions for 72 h (or 7 days in certain cases). Note: The time period between the first and the second treatment is mainly aimed at allowing the activation of plant defense mechanisms by the elicitor action.

3) Second treatment: INOCULATION: After the established period had been completed (3-7 days), aerial parts (petioles and sheets) of the plants that had received the first treatment were sprayed again with spray to dripping point, but this time with a $1.5 \times 10^6$ conidia/ml suspension of isolate M11 of *C. acutatum*, highly virulent for cv. Pajaro. Note: In this stage a live conidial suspension of this strain was always used to trigger a compatible-like interaction (disease control) against the strawberry variety used in the assay (cv. Pajaro) so as to assess the protection degree acquired by the plants against anthracnose disease.

4) Immediately after the second inoculation, plants were taken into a stress chamber (darkness, 100% humidity, 30-32° C.) and kept for 24 h to produce the stomatal opening and favour the germination of virulent pathogen conidia and the penetration of infective hyphae by plant stomas and tricomas.

5) Finally, plants were transferred into the monitoring chamber under conditions that favour the fungal pathogen development, aside from allowing plant growth. Plants were kept under these conditions for 40 days in order to assess the plant symptoms after infection. In this stage, it was determined whether anthracnose disease occurred or not, depending on the protection level accomplished by the different treatments.

The controls used in the assays performed were as follows:

1) Plant sanity control: a lot of cv. Pajaro plants received the identical treatment as the assayed plants but using sterile distilled water in both sprays. Under these conditions, plants should not exhibit disease symptoms.

2) Cross-protection control (control of the inducing capacity of the strain SS71 of *A. strictum*): a lot of cv. Pajaro plants received a first inoculation with a live conidial suspension of the avirulent strain *A. strictum* SS71, at $1.5 \times 10^6$ conidia/ml concentration, and after 72 h (the first 24 h under stress conditions), a second inoculation with live conidia of virulent isolate *C. acutatum* M11 at the same concentration. This experiment was used to control that the avirulent pathogen did not lose the "elicitory" defense response capacity in cv. Pajaro, so that plants do not present disease symptoms.

3) Positive control of *Colletotrichum acutatum* virulence (Control isolate M11 used in the second inoculation): a lot of cv. Pajaro plants received identical treatment as the assayed plants but using sterile distilled water. In this case, plants should develop the disease and wilter within a maximum period of 21 days.

4) Vehicle (liquid culture medium) inactivity positive control (absense of active compounds): to verify that the effect produced by the supernatant used in the assays results from the presence of active compounds exclusively derived from fungal growth and not from the liquid culture medium used, a lot of cv. Pajaro plants received identical treatment as the assayed lot but the first treatment was replaced by spraying with PG medium. The expected results from such treatment was plants developing disease and wilter within a maximum period of 21 days.

5) Positive control of *Acremonium strictum* (strain SS71 producing the elicitor and used in the first inoculation of the cross-protection system): To verify that strain SS71 of *A. strictum* is active and can trigger the disease in genotypes susceptible to the same pathogen, a lot of *F. vesca* wild strawberry plants (highly sensitive) received a single inoculation with a live conidial suspension of such strain at $1.5 \times 10^6$ conidia/ml concentration, which is the same than the one used to get the cross-protection response in cv. Pajaro. Plants develop disease and die around 7 days after inoculation.

6) Innocuity positive control of fractions derived from such strain containing the elicitor or not, if any: in order to verify that extracts and supernatants are free from agents that are phytotoxic or pathogenic for strawberry culture and, therefore, are innocuous and capable of being applied in the field, a lot of *F. vesca* wild strawberry plants highly susceptible to *A. strictum* SS71, was inoculated with each of the fractions from this pathogen cultures (CE, SN or purification subfractions) at the same concentration as the one used to assess the resistance induced in cv. Pajaro. Plants should not exhibit disease symptoms.

Experiments were performed three times and each phytopathological assay was carried out at random with 4 plants per experimental lot and 4 plants per each control. The results shown correspond to the measure (□) of one of the repetitions since the variance ($s^2$) between both repetitions was practically null. Table 2 summarizes the experiments performed and the controls used in this Example.

Data Statistical Analysis

Statistix software (1996 Windows Analytical software) was used. DSR arithmetic mean was studied as position measurement. The software calculated the arithmetic mean of DSR values (average of each repetition four experimental units) corresponding to the forth assessment date (40 days) for each phytopathogenic assay, which were performed with the cultures fractions of *A. strictum* obtained by different treatments. Ctr-PC means Cross-Protection control and Ctr-Ca means positive control of infection of live conidia of *C. acutatum*. The comparison between the different assay means was made by "LSD Test" and "Tukey Test", with 5% significance degree ($\alpha=0.05$) in both cases. To study data dispersion as compared to mean values an Analysis of Variance (ANOVA) was carried out.

Example 6

Elicitor Purification

The elicitor of the present invention was purified from a 21-day culture supernatant of strain SS71 of *A. strictum* grown at 28° C. under continuous white light in PG medium without stirring (SN fraction). After 21 days of culture, the supernatant was collected by centrifugation at 10,000 g (30 min, 4° C.) and filtered through diathomea earth and then through 0.22 μm diameter Millipore membrane. The axenic supernatant was frozen and concentrated 10 times under vacuum (liophilization).

The extract then went through a dialysis tube (12 kDa cut-off) and was further concentrated 4 times by a dehydration treatment using PEG (MW 15000-20000; Sigma) at 4° C. The concentrated extract was subjected to ultrafiltration under nitrogen gas pressure through a molecular filter (30 kDa cut-off; AMICON). The remaining fraction on the membrane was recovered rinsing the membrane surface with Tris-HCl buffer 20 mM (pH 7.5). Elicitor activity was assayed in the retentate and in the filtrate, confirming that all the activity was recovered in the fraction with heavier molecular weight retained by the membrane. The extract containing the active elicitor polypeptide was subjected to two chromatographical separation steps by FPLC: anion exchange and hydrophobic interaction.

TABLE 2

Resistance induction protocol for fractions of cell extract and supernatant

| | No. of plants - strawberry genotype | | First Treatment | Second Treatment |
|---|---|---|---|---|
| Phytopathological Assay | | 4 cv. Pájaro plants | CE<br>SN<br>Purified Frac } of *A. strictum* | Live conidia of *C. acutatum* |
| Controls | Plant Sanity | 4 cv. Pájaro plants | Sterile distilled $H_2O$ | Sterile distilled $H_2O$ |
| | Cross-protection (CP) | 4 cv. Pájaro plants | Live conidia of *A. strictum* | Live conidia of *C. acutatum* |
| | Virulence | 4 *F. vesca* plants | Live conidia of *A. strictum* | — |
| | | 4 cv. Pájaro plants | Sterile distilled $H_2O$ | Live conidia of *C. acutatum* |
| | Inactivity | 4 cv. Pájaro plants | Medio PG | Live conidia of *C. acutatum* |
| | Innocuity | 4 *F. vesca* plants | Product derived from *A. strictum* (CE, SN, Purified Frac.) | — |

In the first chromathography, a Sepharose Q Fast Flow column (Pharmacia-FPLC) was used and in the second a Phenyl Superose HP column (GE-FPLC), both adapted to a FPLC system, monitored at λ=280 nm. Sepharose Q matrix was balanced with Tris HCl 20 mM (pH 7.5) and eluted by increased ionic strength with a discontinuous NaCl gradient in three steps: 0.24 M (8 min), 0.38 M (8 min) and 1 M (10 min); flux rate 1 ml/min. The fraction with elicitory activity corresponding to the column wash (fraction eluted without salt) was collected and subjected to a new chromatography using Phenyl Superose HP column (GE-FPLC) balanced with buffer A: Tris HCl 50 mM (pH 7.5), EDTA (1 mM) and $(NH_4)_2SO_4$ (1.5M). Elution buffer B has the same composition as buffer A but without adding $(NH_4)_2SO_4$. The samples were eluted by decreased ionic strength with a discontinuous gradient of $(NH_4)_2SO_4$ salt divided into 8 steps: 22% B (5 min), 30% B (7 min), 40% (7 min), 50% (7 min), 70% (5 min), 80% (5 min), 90% (5 min), 100% (10 min); flux rate=1 ml/min. The activity of all the fractions was tested by two parallel procedures, analyzing ROS production and the plant protection against pathogen C. acutatum M11.

The fraction eluted at 0.5 M of $(NH_4)_2SO_4$ was visualized as a single peak (peak 7, FIG. 6) and showed both activities analyzed. This peak was collected and desalted twice; first by dialysis with bidistilled water and then by running through an ultra-thin Sephadex G25 column (SIGMA). In each purification step, total proteins were quantified and separated by SDS-PAGE in polyacrylamide gels (12%), dyed with Coomasie Brilliant Blue and/or silver dyeing (Sambrook. et. al, 1989. Molecular cloning, a laboratory manual. Second edition). The desalted fraction eluted from HP column (peak 7) showed a 34 kDa single band on a SDS-PAGE (10%).

Total Protein Determination: Bradford Method

Total protein content in water soluble samples were determined using "Bio-Rad Protein Assay Kit II" based on the Bradford Method (Bradford, 1976. Anal. Biochem. 72, 248-254). The products obtained up to this step were used in the first treatment of Induced Resistance phytopathological assays.

Example 7

Assessment of Elicitory Activity in Each Purification Step

Elicitory activity in each purification step was assessed in strawberry plants analyzing the accumulation of ROS (e.g. $H_2O_2$, and $O_2.^-$) and the protection against anthracnose. In this last case, it was determined by phytopathological assays of the capacity of the different fractions and the purified protein to protect the plant against virulent pathogens. The methodology used for phytopathological assays was explained hereinabove.

Oxidative Burst Assessment:

$H_2O_2$ accumulation was detected by histochemical dyeing with DAB (in strawberry) or by DCFH-DA fluorescent probe (in Arabidopsis) and 02 accumulation was detected by histochemical dyeing with NBT (in both species).

To assess the evolution of the oxidative burst, the generation of hydrogen peroxide and radical superoxide was followed at different time points. For this purpose, strawberry plants (cv. Pajaro) were treated with the elicitor at 10 µg/ml concentration and at different time points, ranging from 0 to 12 hours after treatment (hpt) with the elicitor, 10 proximal or distal leaflets were cut and incubated in a solution containing 0.1% (w/v) DAB, 10 mM MES, pH 3.8 (for peroxide detection) or 0.1% (w/v) NBT, 10 mM sodium azide, 10 mM potassium phosphate (pH 7.8), without adding NADPH (for superoxide detection). Leaves were then incubated from 2 to 8 h in the dark under nitrogen gas pressure. After incubation, the tissue was fixed and bleached by heating in 95% ethanol (w/v), clarified with lactic acid/glycerol/$H_2O$ [3:3:4] for 24 h and mounted on a microscopic slide with 60% glycerol. Histochemical dyeing was observed and documented with an Olympus BH-2 microscope with a digital camera. Plants treated with water and sterile PG medium were used as negative controls.

Hydrogen peroxide intracellular detection in Arabidopsis foliar tissue was performed by DCFH-DA fluorescent probe. A stock solution was prepared at 10 mM concentration in DMSO and working solution was prepared at 40 µM concentration in 10 mM phosphate buffer (pH 7.4). Harvested leaves at different times after elicitor treatment were incubated in DCFH-DA solution in the dark under nitrogen gas pressure for 15 minutes and immediately observed in the fluorescence microscope. For fluorescence detection, microscopic observations and photographing an Olympus BXS1 model microscope, equipped with an U-LH 100HG-like epifluorescence system, a U-MWB2 excitation filter and a digital camera was used. $O_2.^-$ anion detection was performed by histochemical dyeing with NBT as described hereinabove for strawberries.

Quantification of NO and ROS Production in Tomato Cells (Solanum lycopersicon) Cultured in Suspension by Fluorescence:

Four to 5-days-old tomato suspension cell cultures were exposed to different treatments in microtiter plates (for fluorescence measurements). ROS ($H_2O_2$) detection in cells was carried out using the H2DCF diacetate (2',7'-difluorodihydrofluorescein diacetate) fluorescent probe (Molecular Probes). The latter, originally described for phagocytic cells, was adapted and modified to measure the oxidative burst reaction of elicitor-induced cell cultures in suspension by assays in a microplate multichannel automatic fluorescence system. Nitric oxide (NO) quantification in cells was carried out using a DAF-FM diacetate (4-amino-5-methylamino-2', 7'-difluorofluorescein diacetate) fluorescent probe (Molecular Probes).

Ninety µl of cell culture suspension was carefully aliquoted by micropipetting into the wells of a 96-well microtiter plate (Grein Lader) containing 0.025 µM H2DCF-DA or 0.5 µM DAF-FM-DA and 10 µl elicitor at different concentrations (5 or 10 µg/ml final concentration, respectively). The microplate was immediately transferred to the fluorometer to perform measurements. The fluorescence resulting from the oxidative burst reaction produced by the cells was continuously monitored during 30 minutes in a Fluoroskan Acsent microplate fluorometer (Termo Electron Company, Vantaa, Finland) using Chroma D480-40 and D525-30 filters (Chroma Technology Corp, Rockingham, Vt., AS) using λex=480 nm and λem=525 nm.

The fluorescence in each individual well was measured every 20 milli seconds during 2 minutes at 25° C. Between measurements cell suspensions were agitated at 120 RPM with 1 cm rotation at 25° C. All the experiments were performed in triplicate. The resulting fluorescence was expressed as relative ROS production. Control cells were treated with 20 µl pre-incubation medium instead of the elicitor. Xilanase derived from Trichoderma viride was used as ROS and NO induction control at 10 and 100 µg/ml concentration, respectively. Control experiments were also carried out with NO scavengers (cPTIO: 2-(4-carboxyphenyl)-4,4,5, 5-tetramethylimidazoline-1-oxyl-3-oxide potassium salt) and inhibitors of nitric oxide synthase enzyme (Arginine competitors), of NADPH oxidase (Apocinine) and of both enzymes (DPI: diphenyliodonium) to reduce the source of fluorescent species. The treatments with inhibitors were performed incubating cells 30 minutes before the treatment.

Callose Deposition Analysis:

To observe the accumulation of callose, strawberry leaves were treated and dyed. Plants were sprayed with the purified elicitor protein (10 µg/ml) or with water. Leaves were collected 7 days after having been treated with the elicitor (7 dpi). For a positive control, callose deposition was assessed in plants that had been infected with virulent isolate M11 of *C. acutatum* 7 days post-treatment. In this case, leaves were analyzed 48 hours post-inoculation with M11 and thereafter the tissue was clarified and dehydrated with 100% EtOH overnight. Clarified tissue was sequentially transferred into decreasing ethanol solutions in 67 mM $K_2HPO_4$ buffer (pH 12), from 100% to 0% (e.g. 100%, 75%, 50%, 25% and 0%), and then dyed for 1 hour at room temperature with 0.01% blue aniline in 67 mM $K_2HPO_4$ (pH 12). The dyed material was then put in 30% glycerol and examined using ultraviolet epifluorescence in the Olympus BXS1 model microscope, mentioned above.

Determination of Salicylic Acid:

Salicylic acid (SA) was determined in the phloem exudate of leaves from Cv. Pajaro plants sprayed with the elicitor (15 µg/ml) After spraying leaves were harvested at different time points to extract phloem fluid. Experiment controls consisted in plants treated with water (negative), BTH and the virulent isolate M11 of *C. acutatum* as positive controls. At different time points after treatment, phloem exudate was collected by using a micropipette from the petioles of fully expanded leaves of two plants and put together in a single sample. SA concentration was determined for each time point. The exudates were put in cold acidified 100% ethanol (pH 2.5) to pellet proteins and other high molecular weight compounds.

After removing insoluble materials by centrifugation (12,000 g for 15 minutes at 4° C.), ethanolic extracts were transferred into previously weighed microcentrifuge tubes and concentrated to dryness under vacuum using a SVC 200 SpeedVac Sample Concentrator (Savant Instrumentos Co., Farmingale, N.Y.). Once dried, tubes were weighted to calculate the dry weight and samples were resuspended in 250 µl of 30% methanol.

SA separation was performed by HPLC using a C18 reversed phase column (Phenomenex-CV=3.4 ml) balanced in 30% methanol. Runs were performed at 0.5 ml/min mobile phase flow rate and with linear gradient elution with methanol (0-100% in 15 minutes) and then kept in 100% for 20 minutes. SA was spectrophotometrically detected at 280 nm using an UV detector and the SA peak eluted with 100% methanol under the conditions applied. Quantitative analysis was performed by fluorescence using an ISS-PC1 photon counting spectrofluorometer. Salicylic acid concentration was determined in each collected fraction by HPLC ($\lambda ex=296$ nm, $\lambda em=408$ nm). Each punctual data was determined as the average between two replicas of a representative experiment performed in duplicate. Data was expressed as total SA per gram dried weight of exudate.

Self-Fluorescence Detection:

Since it was reported that the defense response development can be associated to the accumulation of self-fluorescent compounds, the presence of self-fluorescent compounds in strawberry leaves after being treated with extracts containing the elicitor was studied, with the pure protein and other solutions used as controls. Treatment was performed by infiltration through the leaflet abaxial side, with a volume of around 50 µl of water or of elicitor (10 µg/ml) using a needleless syringe and the reaction was followed for 96 h by UV epifluorescence (329 nm). Micro photographies were taken with a BH-2 Olympus microscope.

Example 8

Elicitor Molecular Characterization

Microsequencing, Finding Similarities and Alignments

The elicitor polypeptide purified by hydrophobic interaction chromatography by a FPLC system was separated on 12% polyacrylamide gel under denaturalizing conditions using a Tris-Glycine buffer system with SDS and then electro-transferred to an Immobilon-PSQ membrane 0.1 µm pore-diameter in 10 mM CAPS buffer (pH 11).

The band corresponding to the polypeptide was extracted from the gel and subjected to microsequencing by Edman degradation reaction with an 476 Applied Biosystems gas-phase sequencer. The amino acid sequences obtained were compared to known sequences stored in the databases using the BLAST software and the DNAMAN software (version 4-03).

Building an expression library of the elicitor (SS71) producing isolate:

In order to obtain the complete sequence of the elicitor polypeptide, the cDNA transcript was cloned. An expression library was built from the fungal mycelium of a SS71 culture grown in liquid PG medium to stationary phase.

Total RNA from the fungal mycelium of SS71 strain was isolated as follows: each sample (approximately 1.2 grams) was grounded using a mortar and a pestle with liquid $N_2$ and homogenized with 8 ml of extraction buffer preheated to 65° C.

The composition of the extraction buffer used for RNA isolation was the following: Tris-HCl, 100 mM (pH 8), EDTA, 25 mM (pH 8); NaCl, 2.5 M; CTA, 2% PVP, 2%; Spermidine, 0.5 g/l, β-mercaptoethanol, 2%. Once homogenised, the mixture was incubated at 65° C. for 30 min with vigorous stirring every 5 min. After centrifugation at 5,000 g for 10 min at 4° C., the supernatant was filtered through a column QIAShredder (Qiagen) and incubated on ice for one hour. Subsequently, it was further centrifuged at 14,000 g for 10 min at 4° C. to remove any remaining plant material in suspension. The supernatant was purified by two extractions with equal volume of chloroform/isoamyl alcohol (24:1) followed by centrifugation at 14,000 g for 5 min at 4° C. The purified solution was then precipitated with ¼ volume 10 M LiCl and incubated at 4° C. overnight. The following day the precipate was centrifuged at 14,000 g for 45 min at 4° C. and the pellet washed with 70% ethanol and resuspended in 100 µl of bidistilled water treated with DEPC (diethyl pyrocarbonate) 0.1% v/v. Finally, a final cleaning was performed and treatment with "on-column" DNase by using RNAeasy Mini-Kit and RNase-Free DNase Set (Qiagen) kits, respectively, following the manufacturer's instructions. The concentration and purity of the total RNA samples were determined spectrophotometrically by assessing the absorbances at 260, 230 and 280 nm. The total RNA concentration was calculated using the following formula:

$$ARN\ [ng/\mu l] = A_{260} \times \text{Dilution Factor} \times FC$$

wherein FC is the conversion factor (ng/µl): 1 unit of absorbance is around 40 ng/µl for RNA.

The purity with respect to contamination with protein and carbohydrate/polyphenols was estimated by $A_{260}/A_{280}$ and $A_{260}/A_{230}$ relations (both should be ≥2).

Once quantified, samples were immediately used in reverse transcription reactions or stored at −80° C. precipitated with 1/10 volume sodium acetate and 2 volumes of ethanol until used. The corresponding cDNA library was used for PCR amplification reactions.

Isolation of the Elicitor Polypeptide Coding Sequence by PCR Using Degenerateprimers:

Semi-degenerate primers were used to amplify DNA sequences encoding the elicitor protein from *A. strictum.*

Internal and amino terminal sequenced peptides of the elicitor protein were used to design oligonucleotide primers with the lowest possible degree of degeneration (nucleotide variations by position). For such purpose, the regions containing amino acids with less genetic code multiplicity (Example: tryptophan) were used as template thereof, as well as the less conserved amino acid regions in order to avoid obtaining a cDNA coding for a protein homologous to the protein of interest with disease defense elicitory activity.

In the design of the primers the following criteria were taken into account: (1) the most frequently used codons in the species *Acremonium strictum* and other species of *Acremonium* spp., and (2) the codons found in proteins with high sequence identity (obtained from the search performed by BLAST) that belong to other species.

The semi-degenerate primers used were:

NH2 F1 (N1): (SEQ ID NO: 3)
5'-GCNTAYACNACNCARGCNT-3'

NH2 F2: (N2): (SEQ ID NO: 4)
5'-CAGGCBWSBGCBCCBTGG- 3'

InternalF (IF): (SEQ ID NO: 5)
5'-ATYATYGCYGGYATYAACTAYG- 3',

InternalR (IR): (SEQ ID NO: 6)
5'-CRTAGTTRATRCCRGCRATRAT- 3'

COOH R1 (C1): (SEQ ID NO: 7)
5'-RATVACRCCVGTVGIVGCRAT-3'

COOH R2 (C2) (SEQ ID NO: 8)
5'-GTTVGGVGTRCCVWSVGGR-3'

With the aim of selectively isolating the sequence corresponding to the elicitor protein protein, three consecutive amplifications were performed using different combinations of degenerate primers.

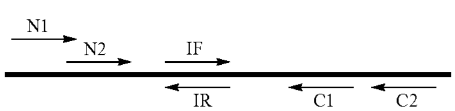

The protocol used for PCR amplification was as follows:

1: An initial amplification was performed to enrich the sample in the product of interest, using the outermost sense and antisense primers (N1 and C2). Twenty ng of cDNA from the expression library was used as template for the PCR reaction.

2: A second Nested PCR type amplification was performed using as template the amplification product obtained from the first PCR diluted 125 times in the reaction mixture (2 μl of dilution 1/10 in 25 μl final volume). In this amplification, the most internal sense and antisense primers were used (N2 and C1). 1.5% agarose gel was used to visualize the amplified product. Candidate bands were selected according to their size in the gel, excised from the gel and purified by a band purification kit.

3: Then, two independent PCR reactions were performed using as template the nucleic acid solution purified in the previous step (4 μl), derived from a single band of 800 bp amplified by Nested PCR. For each amplification reaction internal primer (IF or IR) was used in combination with the amino-terminal primer N2 (N2/IR) or in combination with the carboxy-terminal primer (C1/IF).

The sum of the band sizes obtained with N2/IR and C1/IF should be equal to the weight of the band from which it is derived (~800 bp). Combining primers N2/IR a single band of appropriate intensity of 350 bp is obtained, and with C1/IF a single band of around 500 pb is obtained.

The reactions were carried out in a final reaction volume of 25 μl containing 50 mM KCl, 20 mM Tris-HCl (pH 8.4), 1.5 mM $MgCl_2$, 2 μM of each primer (sense and antisense), 0.2 mM of each dNTP and 0.75 U of Taq DNA polymerase (Invitrogen).

The PCR reaction conditions included an initial denaturation of 10 min at 94° C., followed by 40 consecutive cycles of 45 sec at 94° C. (denaturation), 30 sec at 55° C. (primer hybridization) and 1.5 min at 72° C. (primer elongation). Finally, a final elongation period was added for 10 min at 72° C.

Optimal temperatures for primer hybridization were determined after testing at different temperatures, ranging from 45° C. to 55° C. In addition, different concentrations of $MgCl_2$, concentration of genomic DNA and for each of the primers were tested to optimize reaction conditions. Amplification reactions were performed in a PTC-100 thermocycler from MJ Research Inc.

Separation and Purification of PCR Products:

40 μl of the total reaction volume were grown in TBE/1.5% agarose gels and the amplification products were separated by electrophoresis at 90 V for 1 hour, then dyed with ethidium bromide and visualized with a UV transilluminator (320 nm).

In the second and third amplification step wherein bands with appropriate intensity and size were observed, bands were excised from the gel, purified as explained below and concentrated eluting them in 20 μl volume. A 5 μl aliquot of the purified fragments was used to reamplified them by PCR using the same conditions and the same primers used in the initial amplification. Finally, the presence of the amplicon was verified by electrophoresis.

Cloning and Sequencing of PCR Products:

In all cases, PCR products were directly cloned into cloning vector pCR®2.1 (Invitrogen). The pCR®2.1 vector contains the promoters of the RNA polymerases of T7 and T3 bacteriophages, flanking a multiple cloning region within the coding region of the enzyme β-galactosidase (lac Z). Cloned fragments were sequenced using sequencing primers located upstreams and downstreams of the bacteriophage promoters in accordance with the manufacturer's instructions.

Obtention of Competent *E. coli* Cells:

An aliquot of 100 μl of a pure culture of *Escherichia coli* DH5α in exponential growth phase was inoculated into 40 ml fresh medium and grown at 37° C. and 250 rpm to optical density of 0.6 (OD at 550 nm). The culture obtained under these conditions was kept in an ice bath for 10 min and then centrifuged at 4° C. for 10 min at 7,000 rpm. The supernatant was removed and cells were resuspended in 5 ml of sterile 0.1 M $CaCl_2$. Resuspended cells were left on ice for 20 min, centrifuged as indicated above and after aseptically discarding the supernatant, cells were carefully resuspended in 500

μL of 0.1 M CaCl₂ precooled at 4° C. The cell suspension was stored in a refrigerator at 4° C. overnight.

Transformation:

The transformation of competent cells was performed by thermal shock in accordance with Sambrock et al. (Sambrook et al., 1989. Molecular cloning, a laboratory manual. Second edition).

Verification of Inserts and Sequencing:

For each cloning event, 10 white colonies were selected for further analysis, and grown o/n on LB agar plates supplemented with ampicillin 100 μg/ml. From these colonies, liquid cultures were produced in 8 to 10 mL of LB medium with ampicillin (100 μg/ml). Plasmids were then extracted and purified according to Sambrook et al. (Sambrook et al., 1989. Molecular cloning, a laboratory manual. Second edition).

Plasmids were eluted in 100 μl of sterile bidistilled water and the integrity and amount of DNA was verified as described in section 2.3. Identification of positive clones (verification of inserts) was conducted by PCR technique using T3 (5'-ATTAACCCTCACTAAAGGGA-3') (SEQ ID NO: 9) and T7 (5'-TAATACGACTCACTATAGGG-3') (SEQ ID NO: 10) universal primers in a reaction volume of 20 μL containing 1× Taq polymerase buffer without Mg, 2 mM MgCl₂, 0.5 μM of each primer, 0.2 mM of each dNTP, 1 U of Taq DNA polymerase (Promega) and 50 ng of plasmid DNA. Reaction conditions were: denaturation for 2 min at 95° C., 30 cycles of 30 sec at 95° C., 30 sec at 52° C. and 1 min at 72° C. followed by a final extension of 5 min at 72° C. PCR products were separated on 1% agarose gels in 0.5×TBE, dyed with ethidium bromide and visualized by UV light. The same primers used for insert verification were used to sequence each insert in both directions.

Sequence Editing and DNA-Protein Homology Search

The sequences obtained were initially analyzed with the VecScreen and ORF Finder algorithms (http://.ncbi.nim.nih.gov/) in order to remove vector sequences and to identify potential open reading frames, respectively. DNAMAN software version 5.2.2 (Lynnon Biosoft, Quebec, Canada) was used for assemblies of nucleotide sequences and obtention of the deduced amino acid sequences. The nucleotide and amino acid sequences were compared with sequences deposited in the GenBank NR database using Blast X and Blast P heuristic algorithms. The expected threshold value was set at 0.0001 (e-value), which is a value empirically determined to filter expected alignments at random due to the size of the search space. By CDSearch (NCBI), SMART 5 and Pfam (Sanger Institute) programs the presence of structural motifs and/or conserved domains was determined.

Specific Primer Design

To confirm the sequence corresponding to the mature cDNA transcript of the elicitor protein, specific primers were designed from the consensus nucleotide sequence obtained from the 10 selected clones. In addition, less conserved regions of the subtilisin family, which did not contain variable nucleotides among the sequences of the different clones, were also selected. Primers were designed using the software DNAMAN version 5.2.2 program.

```
                                    (SEQ ID NO: 11)
    GSPvar-F:      5'-GGCCCAACTGGCTACACC-3'

(SEQ ID NO: 12)
    GSPVar-R:      5'-ATGGCGACGATGCGGTTG-3'
```

Complete Sequencing of the cDNA Using RACE-PCR Methodology

The complete sequence of the complementary DNA (cDNA) transcribed or the mature transcript corresponding to the elicitor protein was obtained by the RACE technique (Rapid Amplification of cDNA Ends) according to Frohman et al. (Frohman et al., 1988. Proc. Natl. Acad. Sci. USA. 85, 8998-9002).

A GeneRacer system by Invitrogen was used, which is based on a technique that uses RNA ligase (RLM-RACE: "RNA ligase-mediated Rapid Amplification of cDNA Ends"), following the manufacture's instructions.

A RACE-like expression library of the elicitor-producing pathogenic isolate *A. strictum* SS71, comprised of the first strands of the cDNA with annealing sites for GeneRacer primers of the 5' and 3' ends was obtained. Briefly, the GeneRacer technology system is based on the treatment of isolated mRNA with a phosphatase (CIP) which removes the phosphate groups present at the 5' end of the partially degraded messengers, so that only those with complete sequence and protected by cap or a "Cap" structure can continue with the cloning protocol. Then, the mRNA is treated with a pyrophosphatase (TAP), which removes this "cap" from the undegraded mRNA leaving a phosphate group in the 5'position which can be bound by a RNA oligonucleotide with a specific sequence which will be used for the amplification process typical of the RACE technique.

Design of Specific Primers for RACE

The design of gene-specific primers (GSP"'), that anneal to the 5' and 3' ends of the gene fragment of interest, was carried out using the DNAMAN program version 5.2.2 (Lynnon Biosoft, Québec, Canada) following the criteria below:

High temperature annealing (>72° C.) which was achieved by the length of the primers (24-28 nucleotides) and high GC content (50-70%).

Low GC content to the 3' end of the primers (no more than two G or C residues in the last 5 bases)

Absence of self-complementarity within the primer and absence of complementary sequences to the GeneRacer primers used.

Design of nested primers (Nested RACE) located within the first amplified sequence in order to increase specificity by using nested PCR technique, which consists in a second amplification using as template the product of the first amplification. These internal primers characteristics should be similar to those mentioned above.

To obtain the nucleotide sequence of 5' and 3' ends of the mature transcript corresponding to the elicitor protein using RACE-like technology, specific primers were designed according to the requirements described hereinabove from the sequence confirmed by cloning with GSPvar-F and GSPvar-R primers.

The primers used to obtain the 5' end were:

```
The primers used to obtain the 5'end were:
GSP RACE-R (GSP-5):
                                    (SEQ ID NO: 13)
5'-GATGTTGTTGTCGATCAAGGACTTGG-3'

GSP RACE Nested-R (GSPN-5):
                                    (SEQ ID NO: 14)
5'-TGCCTTGGTAGGAGACAAGCTGGAA-3'

The primers used to obtain the 3' end were:
GSP RACE-F (GSP-3):
                                    (SEQ ID NO: 15)
5'-AGCTTGTCTCCTACCAAGGCAGCAA-3'
```

-continued

GSP RACE Nested-F (GSPN-3):
(SEQ ID NO: 16)
5'-GGCCAAGTCCTTGATCGACAACAAC-3'

The primers provided by RACE kit are as follows:
GeneRacer ™ 5' (R-5):
(SEQ ID NO: 17)
5'-CGACTGGAGCACGAGGACACTGA-3'

GeneRacer ™ 5' Nested (RN-5):
(SEQ ID NO: 18)
5'-GGACACTGACATGGACTGAAGGAGTA-3'

GeneRacer ™ 3' (R-3):
(SEQ ID NO: 19)
5'-GCTGTCAACGATACGCTACGTAACG-3'

GeneRacer ™ 3' Nested (RN-3):
(SEQ ID NO: 20)
5'-CGCTACGTAACGGCATGACAGTG-3'

The following is a scheme with the relative location of all primers described in the RACE-PCR procedure outlined above:

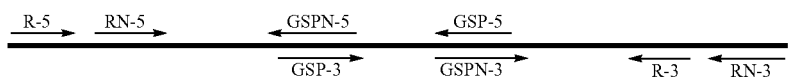

Amplifications by PCR

In order to minimize non-specific primer annealing ("misspriming") for the amplification reactions Platinum Taq DNA Polymerase High Fidelity enzyme (Invitrogen) was used in accordance to the manufacturer's instructions.

Reactions were carried out in a final volume of 50 µl containing 1×PCR buffer, 0.2 mM of each dNTP, 2 mM MgSO$_4$, 0.6 µM of 5' or 3'GeneRacer primer, 0.2 µM of 5' or 3' specific primer (GSP-5 or GSP-3 respectively), 2.5 U of Platinum Taq DNA Polymerase and 1 µl of a ⅕ dilution of the product of reverse transcription of the RACE expression library constructed from the isolated producer SS71. The thermocycler program used to apply the technique of "touchdown" was:

Initial denaturation: 94° C. for 2 minutes
5 cycles of 94° C. for 30 seg and 72° C. for 4 min (1 min/kb DNA)
5 cycles of 94° C. for 30 seg and 70° C. for 4 min
25 cycles of 94° C. for 30 seg, 66° C. for 30 seg and 68° C. for 4 min
Final extension: 68° C. for 10 min PCR products were separated and visualized on 1% agarose gels as described in 2.4.

Nested PCR

Amplifications were performed by nested PCR from the first amplification product. The reactions were carried out in a final volume of 50 µl containing 1×PCR buffer, 0.2 mM of each dNTP, 2 mM MgSO$_4$, 0.2 µM of 5' or 3' GeneRacer Nested Primer, 0.2 µM of 5' or 3' of the specific primer (GSPN-5 or GSPN-3, respectively), 1 U de Platinum Taq DNA Polymerase and 1 µl of a ¹⁄₁₀ dilution of initial PCR product. The PCR program used was:

Initial denaturation: 94° C. for 2 minutes
25 cycles of 94° C. for 30 seg, 66° C. for 30 seg and 68° C. for 4 min
Final extension: 68° C. for 10 min PCR products were separated and visualized on 1% agarose gels. If there was more than one band, each of these was separated from the gel, purified and cloned as described above. Finally, 3 recombinant clones were selected for each amplification/transformation event, which were purified and sequenced in both directions using T3 and T7 universal primers as described above.

Example 9

Determination of Subtilisin-Like Proteolytic Activity

Since the analysis of nucleotide and amino acid sequences suggested that the protein might be a subtilisin-like protease, assays were conducted to determine proteolytic activity in vitro. For such purpose, the ability to hydrolyze the chromogenic peptide substrate N-Suc-Ala-Ala-Pro-Phe-pNA, specific for trypsin/subtilisin, was assessed. The proteolytic cleavage causes the release of p-nitroanilide that absorbs at $\lambda$=405 nm (Moallaei et al., 2006. Mycopathologia 161, 369-375). Optimal conditions for the enzymatic activity of the elicitor protein were first determined (temperature, pH). To further characterize and confirm the protease function, the effect of specific inhibitors for various proteases on the proteolytic activity of the elicitor of the invention derived from SS71 was also studied.

Example 10

Treatment of Strawberry Plants with Conidia of the Strain SS71 of A. strictum

Conidia of the strain SS71 of A. strictum were resuspended as shown in Example 2. They were sprayed on strawberry plants of cultivars Pajaro, Chandler, Milsei, Camarosa and Sweet Charlie at a concentration of $10^5$, $10^6$ and $10^7$ conidia/ml.

Induction of the defense response in plants was assessed by monitoring oxidative burst by measuring accumulation of $H_2O_2$ y $O_2$, determine SA increase, production of PR-proteins, plant cell wall thickening, translocation of the signal from a leaf to the rest of the plant (systemic response), protection against different virulent isolates of the genus Colletotrichum spp. causing anthracnose and other strawberry pathogens (Botrytis cinerea, Xanthomonas fragariae), resistance to subsequent infections with virulent isolates and long-term response over time (durability or persistence over time).

Example 11

Plant Treatment with CE Extract of the Strain SS71 of A. strictum

Conidial extract (CE) was obtained by sonication of conidia from the strain SS71 of A. strictum as shown in Example 3. The aerial parts of strawberry plants were sprayed with CE at a concentration of 1.5 µs protein/ml. Interestingly, CE retains its activity when diluted 12 times reaching a final concentration of 0.12 µg/ml protein.

Induction of plant defense responses in strawberries was assessed by protection against different virulent isolates a the genus *Colletotrichum* spp. causing anthracnose in different strawberry genotypes (Pajaro, Chandler Milsei and Camarosa) and other strawberry pathogens (*B. cinerea* and *X. fragariae*). In addition, ROS production ($H_2O_2$ y $O_2$) was observed when strawberry plants were treated with CE at a concentration 0.12 µg/ml.

Example 12

Plant Treatment with SN Extract of the Strain SS71 of *A. strictum*

The cell-free supernatant (SN) was recovered from a culture of isolate SS71 of *A. strictum* grown at 28° C., without stirring at continuous white light until reaching stationary phase (21 days) as shown in Example 4. Aerial parts of strawberry plants were sprayed with 1×SN (undiluted) corresponding to a total concentration of 8.43 µg protein/ml. SN retained its elicitory activity when diluted about 21 times reaching a final concentration of only 0.4 µg protein/ml.

The induction of plant defense responses in strawberries was assessed by disease resistance, evaluated by the protection against different virulent isolates of the genus *Colletotrichum* spp. causing anthracnose in different strawberry genotypes (Pajaro, Chandler Milsei and Camarosa) and other strawberry pathogens (*B. cinerea* and *X. fragariae*) in cv. Pajaro. Anthracnose resistance is obtained by treating a single leaf of the plant, generating a systemic protective response.

When cv. Pajaro strawberry plants were treated with SN 1× (8.43 µs protein/ml) accumulation of ROS ($H_2O_2$ y $O_2$) and microscopic HR was observed not only in treated tissue but also in untreated leaves (micro bursts and micro systemic HR). Other defense responses observed were SA increase, plant cell wall thickening due to accumulation of lignin and accumulation of self-fluorescent species resulting from accumulation of compounds of the phenylpropanoid pathway. These responses are also observed when performing the application of axenic SN diluted 5 times (~2 µs protein/ml). When tomato cell cultures (*Solanum lycopersicon*) were treated with SN 1× (8.43 µg protein/ml) exacerbated accumulation of ROS and NO was observed. In addition, SN 1× (8.43 µs protein/ml) resulted in deposition of callose in cell wall and accumulation of ROS ($H_2O_2$ y $O_2$) in plants of *A. thaliana*.

Example 13

Plant Treatment with the Purified Elicitor Polypeptide of the Strain SS71 of *A. strictum*

The subtilisin-like elicitor polypeptide was purified from the cell-free supernatant (SN) of a culture of the isolate SS71 of *A. strictum* as shown in Example 7. Aerial parts of strawberry plants were sprayed with such elicitor polypeptide at varying concentrations between 2.5 to 15 µg/ml of polypeptide, depending on the studied defense response.

The induction of plant defense responses was assessed by disease resistance when the polypeptide was applied at a minimum concentration of 2.5 µg/ml and an optimal concentration of 10 µg/ml. The protection against different virulent isolates of *Colletotrichum* spp. causing anthracnose in different strawberry genotypes (broad spectrum response) and against other strawberry pathogens (*Botrytis cinerea*, *X. fragariae*) in cv. Pajaro was observed. Anthracnose resistance in particular is achieved by treating a single leaf of the plant with the elicitor polypeptide at a concentration 5 µg/ml, which is a systemic protective response.

When strawberry plants of cv. Pajaro were treated with the elicitor polypeptide at a concentration of 10 µg/ml, accumulation of ROS ($H_2O_2$ y $O_2$) was observed and microscopic HR including in untreated foliar tissue (micro bursts and micro systemic HR), plant cell wall thickening due to accumulation of callose and lignin; accumulation of self-fluorescent species derived from the phenylpropanoid pathway and induction of PR protein encoding genes (chitinases, glucanases). Treatment with the elicitor polypeptide at a concentration of 15 µg/ml induced SA accumulation. On the other hand, exacerbated accumulation of ROS and NO was observed in cell cultures of tomato (*Solanum lycopersicon*) treated with the elicitor polypeptide at a final concentration of 10 and 5 µg/ml, respectively. In addition, elicitor polypeptide at a concentration of 10 µg/ml is capable of inducing callose accumulation in the plant cell wall and oxidative burst ($H_2O_2$ y $O_2$) in plants of *A. thaliana*.

BIBLIOGRAPHY

Adikaram, N. K. B.; Joyce, D. C. and Terry, L. A. (2002). Biocontrol activity and induced resistance as a possible mode of action for *Aureobasidium pullulans* against grey mould of strawberry fruit. Australasian Plant Pathology 31(3), 223-229.

Bent, A. and Mackey, D. (2007). Elicitors, Effectors and R Genes: The New Paradigm and Lifetime supply of Questions. Annu. Rev. Phytopathol. 45, 399-436.

Bradford, M. (1976). A rapid and sensitive method for the determination of microgram quantities of protein utilizing the principle of protein-dye binding. Anal. Biochem. 72, 248-254.

Delp B. R. and Milholland R. D. (1980). Evaluating strawberry plants for resistance to *Colletotrichum fragariae*. Plant Disease 64, 1071-1073

Eikemo, H.; Stensvand, A. and Tronsmo, A. M. (2003). Induced Resistance as a Possible Means to Control Diseases of Strawberry Caused by *Phytophthora* spp. Plant Disease 87, 345-350.

Felix, G., Grosskopof, D. G., Regenass, M., Basse, C. W. and Boller, T. (1991) Elicitor-Induced Ethylene Biosynthesis in Tomato Cells. Plant Physiol. 97, 19-25

Frohman M. A., Dush M. K. and Martin G. R. (1988) Rapid production of full-length cDNAs from rare transcripts: amplification using a single gene-specific oligonucleotide. Proc. Natl. Acad. Sci. USA. 85, 8998-9002.

Fulton, R. W. (1986). Practices and precautions in the use of cross-protection for virus disease control. Annu. Rev. Phytopathol. 24, 67-81.

Hunt, M and Ryals, J. (1996). Systemic acquired resistance signal transduction. Crit. Rev. Plant Sci. 15, 583-606.

Kamoun, S. (2006). A Catalogue of the Effector Secretome of Plant Pathogenic Oomycetes. Annu. Rev. Phytopathol. 44, 41-60.

Keen, N. T. (1990). Gene-for-gene complementarity in plant-pathogen interactions. Annu. Rev. Genet. 24, 447-463.

Knogge, W. (1996). Fungal Infection of Plants. The Plant Cell 8, 1711-1722.

Kuć J. (1982) Induced immunity to plant disease. BioScience 32, 854-860

Liu C, Matsushita Y, Shimizu K, Makimura K, Hasumi K. (2007) Activation of prothrombin by two subtilisin-like serine proteases from *Acremonium* sp. Biochem Biophys Res Commun. 2007 Jun. 22; 358(1):356-62. Epub 2007 Apr. 30.

Moallaei, H., Zaini, F., Larcher, G., Beucher, B. and Bouchara, J. P. (2006). Partial purification and characterization of a 37 kDa extracellular proteinase from *Trichophyton vanbreuseghemii*. Mycopathologia 161, 369-375

Nürnberger, T. (1999). Signal perception in plant pathogen defense. Cell Mol. Life Sci. 55, 167-182.

Salazar, S. M.; Diaz Ricci, J. C. y Castagnaro, A. P. (2001). Caracterización de la Protección Cruzada en Frutilla (*Fragaria ananassa* Duch.) como una estrategia de Biocontrol de la Antracnosis. IV Encuentro Latinoamericano de Biotecnologia Vegetal (REDBIO 2001). Goiania, Brasil.

Salazar, S. M.; Diaz Ricci, J. C. y Castagnaro A. P. (2002). Respuesta defensiva en fresa (*Fragaria ananassa*) desencadenada por un patógeno avirulento. V Simposio Nacional de Biotecnologia Vegetal (REDBIO Argentina 2002). Buenos Aires, Argentina.

Sambrook, J., Fritsch, E. F., and Maniatis, T. (1989). Molecular cloning, a laboratory manual. Second edition. Cold Spring Harbor Laboratory Press, New York.

Stergiopoulos, I. and de Wit, P. J. G. M. (2009). Fungal Effector Proteins. Annu. Rev. Phytopathol. 47, 233-263.

The invention claimed is:

1. A nucleotide sequence encoding for a polypeptide comprising the amino acid sequence SEQ ID NO: 2, wherein said nucleotide sequence comprises the sequence SEQ ID NO: 1 or sequences at least 90% similar to sequence SEQ ID NO: 1, and wherein the polypeptide has inducing activity for plant defense, and wherein the nucleotide sequence is a cDNA.

2. A microorganism comprising the nucleotide sequence according to claim 1.

* * * * *

SEQUENCE LISTING

```
<160> NUMBER OF SEQ ID NOS: 29

<210> SEQ ID NO 1
<211> LENGTH: 853
<212> TYPE: DNA
<213> ORGANISM: Acremonium strictum

<400> SEQUENCE: 1
gcgtacacca cccaggccag tgcccctgg ggtcttgccc gtatctctac tcgtcagcgt    60
ggcccaactg gctacaccta cgacgacagc gccggcgcag gaacctgctc ctacatcatt   120
gacaccggca tccaggctaa ccaccccaac ttcggtggcc gtgctttcca gcttgtctcc   180
taccaaggca gcaacgccga cggtaatggc cacggcactc acgttgccgg taccatcggt   240
tctaccacct acggtgtcgc caagcgcacc accctcctcg gcgtcaaggt cctcagcgac   300
tccggctccg gttccacctc cggtatcatc gccggcatca actacgtcgt cagcgactct   360
cgctcccgca gctgccccaa cggttccgtc gccaacatgt cgctcggcgg aggctactct   420
gcttcgctca acagcgcggc caagtccttg atcgacaaca acatcttcct tgccgttgct   480
gccggtaacg agaaccagaa cgccgccaat gtctcccctg cttctgagcc gactgtctgc   540
actgttggtg cgaccacttc tgccgacgcc aaggcttctt tctccaacta cggctccggt   600
gtcgacatct tcgctcctgg tcagagcatt ctatccacct ggattggcag cagcaccaac   660
accatctctg gcacctccat ggcttctccc cacatcgccg tcttgctgc ttaccttgct   720 ggtcttgagg gcttccccgg tgcccaggcc ctgtgcaacc gcatcgtcgc cctcgctacc   780
actggtgtca tcaccggtct gcccagcggt accccaacc gccttgcctt caacggcaac   840
ccctctggtt aaa                                                      853

<210> SEQ ID NO 2
<211> LENGTH: 274
<212> TYPE: PRT
<213> ORGANISM: Acremonium strictum

<400> SEQUENCE: 2

Ala Tyr Thr Thr Gln Ala Arg Ala Pro Trp Gly Leu Ala Arg Ile Ser
1               5                   10                  15

Thr Arg Gln Arg Gly Pro Thr Gly Tyr Thr Tyr Asp Asp Ser Ala Gly
                20                  25                  30

Ala Gly Thr Cys Ser Tyr Ile Ile Asp Thr Gly Ile Gln Ala Asn His
            35                  40                  45

Pro Asn Phe Gly Gly Arg Ala Phe Gln Leu Val Ser Tyr Gln Gly Ser
        50                  55                  60

Asn Ala Asp Gly Asn Gly His Gly Thr His Val Ala Gly Thr Ile Gly
65                  70                  75                  80

Ser Thr Thr Tyr Gly Val Ala Lys Arg Thr Thr Leu Leu Gly Val Lys
                85                  90                  95
```

-continued

```
Val Leu Ser Asp Ser Gly Ser Gly Thr Ser Gly Ile Ile Ala Gly
            100                 105                 110
Ile Asn Tyr Val Val Ser Asp Ser Arg Ser Arg Ser Cys Pro Asn Gly
        115                 120                 125
Ser Val Ala Asn Met Ser Leu Gly Gly Gly Tyr Ser Ala Ser Leu Asn
    130                 135                 140
Ser Ala Ala Lys Ser Leu Ile Asp Asn Asn Ile Phe Leu Ala Val Ala
145                 150                 155                 160
Ala Gly Asn Glu Asn Gln Asn Ala Ala Asn Val Ser Pro Ala Ser Glu
                165                 170                 175
Pro Thr Val Cys Thr Val Gly Ala Thr Thr Ser Ala Asp Ala Lys Ala
            180                 185                 190
Ser Phe Ser Asn Tyr Gly Ser Gly Val Asp Ile Phe Ala Pro Gly Gln
        195                 200                 205
Ser Ile Leu Ser Thr Trp Ile Gly Ser Ser Thr Asn Thr Ile Ser Gly
    210                 215                 220
Thr Ser Met Ala Ser Pro His Ile Ala Gly Leu Ala Ala Tyr Leu Ala
225                 230                 235                 240
Gly Leu Glu Gly Phe Pro Gly Ala Gln Ala Leu Cys Asn Arg Ile Val
                245                 250                 255
Ala Ile Ala Thr Thr Gly Val Ile Lys Gly Ile Pro Ser Gly Thr Pro
            260                 265                 270
Asn Arg
```

<210> SEQ ID NO 3
<211> LENGTH: 19
<212> TYPE: DNA
<213> ORGANISM: Artificial Sequence
<220> FEATURE:
<223> OTHER INFORMATION: NH2 F1 (N1)
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 3
gcntayacna cncargcnt                                               19

<210> SEQ ID NO 4
<211> LENGTH: 18
<212> TYPE: DNA
<213> ORGANISM: Artificial Sequence
<220> FEATURE:
<223> OTHER INFORMATION: NH2 F2 (N2)

<400> SEQUENCE: 4
caggcbwsbg cbccbtgg                                                18

<210> SEQ ID NO 5
<211> LENGTH: 22
<212> TYPE: DNA

```
<213> ORGANISM: Artificial Sequence
<220> FEATURE:
<223> OTHER INFORMATION: InternoF (IF)

<400> SEQUENCE: 5
atyatygcyg gyatyaacta yg                                              22

<210> SEQ ID NO 6
<211> LENGTH: 22
<212> TYPE: DNA
<213> ORGANISM: Artificial Sequence
<220> FEATURE:
<223> OTHER INFORMATION: InternoR (IR)

<400> SEQUENCE: 6
crtagttrat rccrgcratr at                                              22

<210> SEQ ID NO 7
<211> LENGTH: 21
<212> TYPE: DNA
<213> ORGANISM: Artificial Sequence
<220> FEATURE:
<223> OTHER INFORMATION: COOH R1 (C1)

<400> SEQUENCE: 7
ratvacrccv gtvgtvgcra t                                               21

<210> SEQ ID NO 8
<211> LENGTH: 19
<212> TYPE: DNA
<213> ORGANISM: Artificial Sequence
<220> FEATURE:
<223> OTHER INFORMATION: COOH R2 (C2)

<400> SEQUENCE: 8
gttvggvgtr ccvwsvggr                                                  19

<210> SEQ ID NO 9
<211> LENGTH: 20
<212> TYPE: DNA
<213> ORGANISM: Artificial Sequence
<220> FEATURE:
<223> OTHER INFORMATION: T3

<400> SEQUENCE: 9
attaaccctc actaaaggga                                                 20

<210> SEQ ID NO 10
<211> LENGTH: 20
<212> TYPE: DNA
<213> ORGANISM: Artificial Sequence
<220> FEATURE:
<223> OTHER INFORMATION: T7

<400> SEQUENCE: 10
taatacgact cactataggg                                                 20

<210> SEQ ID NO 11
<211> LENGTH: 18
<212> TYPE: DNA
<213> ORGANISM: Artificial Sequence
<220> FEATURE:
<223> OTHER INFORMATION: GSPvar-F

<400> SEQUENCE: 11
ggcccaactg gctacacc                                                   18
```

<210> SEQ ID NO 12
<211> LENGTH: 18
<212> TYPE: DNA
<213> ORGANISM: Artificial Sequence
<220> FEATURE:
<223> OTHER INFORMATION: GSPvar-R

<400> SEQUENCE: 12
atggcgacga tgcggttg                                              18

<210> SEQ ID NO 13
<211> LENGTH: 26
<212> TYPE: DNA
<213> ORGANISM: Artificial Sequence
<220> FEATURE:
<223> OTHER INFORMATION: GSP RACE-R (GSP-5)

<400> SEQUENCE: 13
gatgttgttg tcgatcaagg acttgg                                     26

<210> SEQ ID NO 14
<211> LENGTH: 25
<212> TYPE: DNA
<213> ORGANISM: Artificial Sequence
<220> FEATURE:
<223> OTHER INFORMATION: GSP RACE Nested-R (GSPN-5)

<400> SEQUENCE: 14
tgccttggta ggagacaagc tggaa                                      25

<210> SEQ ID NO 15
<211> LENGTH: 25
<212> TYPE: DNA
<213> ORGANISM: Artificial Sequence
<220> FEATURE:
<223> OTHER INFORMATION: GSP RACE -F (GSP-3)

<400> SEQUENCE: 15
agcttgtctc ctaccaaggc agcaa                                      25

<210> SEQ ID NO 16
<211> LENGTH: 25
<212> TYPE: DNA
<213> ORGANISM: Artificial Sequence
<220> FEATURE:
<223> OTHER INFORMATION: GSP RACE Nested-F (GSPN-3)

<400> SEQUENCE: 16
ggccaagtcc ttgatcgaca acaac                                      25

<210> SEQ ID NO 17
<211> LENGTH: 23
<212> TYPE: DNA
<213> ORGANISM: Artificial Sequence
<220> FEATURE:
<223> OTHER INFORMATION: GeneRacer 5' (R-5)

<400> SEQUENCE: 17
cgactggagc acgaggacac tga                                        23

<210> SEQ ID NO 18
<211> LENGTH: 26
<212> TYPE: DNA
<213> ORGANISM: Artificial Sequence
<220> FEATURE:

-continued

<223> OTHER INFORMATION: GeneRacer 5' Nested (RN-5)

<400> SEQUENCE: 18
ggacactgac atggactgaa ggagta                                    26

<210> SEQ ID NO 19
<211> LENGTH: 25
<212> TYPE: DNA
<213> ORGANISM: Artificial Sequence
<220> FEATURE:
<223> OTHER INFORMATION: GeneRacer 3' (R-3)

<400> SEQUENCE: 19
gctgtcaacg atacgctacg taacg                                     25

<210> SEQ ID NO 20
<211> LENGTH: 23
<212> TYPE: DNA
<213> ORGANISM: Artificial Sequence
<220> FEATURE:
<223> OTHER INFORMATION: GeneRacer 3' Nested (RN-3)

<400> SEQUENCE: 20
cgctacgtaa cggcatgaca gtg                                       23

<210> SEQ ID NO 21
<211> LENGTH: 11
<212> TYPE: PRT
<213> ORGANISM: Acremonium strictum

<400> SEQUENCE: 21

Tyr Thr Ala Ser Thr Arg Pro Gly Thr Ala Gln
1               5                   10

<210> SEQ ID NO 22
<211> LENGTH: 12
<212> TYPE: PRT
<213> ORGANISM: Acremonium chrysogenum

<400> SEQUENCE: 22

Ile Gln Ala Glu Ser Gln Glu Pro Gly Thr Ala Asp
1               5                   10

<210> SEQ ID NO 23
<211> LENGTH: 7
<212> TYPE: PRT
<213> ORGANISM: Acremonium sp.

<400> SEQUENCE: 23

Asp Val Thr Thr Ala Glu Tyr
1               5

<210> SEQ ID NO 24
<211> LENGTH: 25
<212> TYPE: PRT
<213> ORGANISM: Acremonium sp.

<400> SEQUENCE: 24

Asp Ser Glu Leu Glu Lys Ala Thr Leu Ser Phe Ala Thr Phe Asn Lys
1               5                   10                  15

Ala Ala Glu Glu Val Asp Ala Thr Asn
            20                  25

<210> SEQ ID NO 25

```
<211> LENGTH: 13
<212> TYPE: PRT
<213> ORGANISM: Acremonium chrysogenum

<400> SEQUENCE: 25

Ala Leu Val Thr Gln Ala Thr Pro Ser Ser Tyr Ala Leu
1               5                   10

<210> SEQ ID NO 26
<211> LENGTH: 4
<212> TYPE: PRT
<213> ORGANISM: Acremonium sp.

<400> SEQUENCE: 26

Tyr Val Ser Gly
1

<210> SEQ ID NO 27
<211> LENGTH: 10
<212> TYPE: PRT
<213> ORGANISM: Acremonium strictum

<400> SEQUENCE: 27

Ala Tyr Thr Thr Gln Ala Ser Ala Pro Trp
1               5                   10

<210> SEQ ID NO 28
<211> LENGTH: 25
<212> TYPE: PRT
<213> ORGANISM: Acremonium strictum

<400> SEQUENCE: 28

Val Leu Ser Asp Ser Gly Ser Gly Ser Thr Ser Gly Ile Ile Ala Gly
1               5                   10                  15

Ile Asn Tyr Val Val Ser Asp Ser Arg
            20                  25

<210> SEQ ID NO 29
<211> LENGTH: 20
<212> TYPE: PRT
<213> ORGANISM: Acremonium strictum

<400> SEQUENCE: 29

Ile Val Ala Ile Ala Thr Thr Gly Val Ile Lys Gly Ile Pro Ser Gly
1               5                   10                  15

Thr Pro Asn Arg
            20
```